United States Patent [19]

Wythes

[11] Patent Number: 5,607,960
[45] Date of Patent: Mar. 4, 1997

[54] INDOLE DERIVATIVES AS 5-HT1-LIKE AGONISTS FOR USE IN MIGRAINE

[75] Inventor: Martin J. Wythes, Sandwich, United Kingdom

[73] Assignee: Pfizer Inc., New York, N.Y.

[21] Appl. No.: 532,573

[22] PCT Filed: Apr. 11, 1994

[86] PCT No.: PCT/EP94/01121

§ 371 Date: Oct. 20, 1995

§ 102(e) Date: Oct. 20, 1995

[87] PCT Pub. No.: WO94/24127

PCT Pub. Date: Oct. 27, 1994

[30]   Foreign Application Priority Data

Apr. 22, 1993 [GB] United Kingdom ............... 9308360
Nov. 27, 1993 [GB] United Kingdom ............... 9324433

[51] Int. Cl.$^6$ ............ A61K 31/405; C07D 401/04; C07D 401/06
[52] U.S. Cl. ............ 514/414; 514/415; 514/419; 514/323; 514/339; 514/210; 546/20; 546/277.4; 548/466; 548/492; 548/493; 548/494; 548/511
[58] Field of Search ............ 548/466, 492, 548/493, 494, 511; 514/414, 415, 419, 323, 339; 546/20, 273

[56]   References Cited

FOREIGN PATENT DOCUMENTS

| | | |
|---|---|---|
| 0237678 | 9/1987 | European Pat. Off. . |
| 0303506 | 8/1988 | European Pat. Off. . |
| 9206973 | 4/1992 | WIPO . |

OTHER PUBLICATIONS

M. Von Strandtmann, et al., *J. Med. Chem.*, 6 (1963), pp. 719–725.

R. A. Glennon, *J. Med. Chem.*, 22(4), pp. 428–432 (1979).

Chem Ab. 77 (13), B. E. Leonard, et al., *Neuropharm*, 11 (3), pp. 373–384 (1972).

A. Agarwal, et al., *J. Med. Chem.*, 36 (25), pp. 4006–4014 (1993).

*Primary Examiner*—Joseph McKane
*Attorney, Agent, or Firm*—Peter C. Richardson; Paul H. Ginsburg; Grover F. Fuller, Jr.

[57]   ABSTRACT

The present invention relates to 3,5-disubstituted indole compounds which are selective agonists which act on 5-hdroxytryptamine receptors useful in the treatment of migraine.

9 Claims, No Drawings

INDOLE DERIVATIVES AS 5-HT1-LIKE AGONISTS FOR USE IN MIGRAINE

This applicaiton is a 371 of PCT/EP 94/01121 filed Apr. 11, 1994.

The present invention relates to indole derivatives which act on 5-hydroxytryptamine (5-HT) receptors.

More particularly the present invention relates to 3,5-disubstituted indoles which are selective agonists at the "5-$HT_1$-like" subtype of the 5-hydroxytryptamine receptor. Such "5-$HT_1$-like" receptors are present in the carotid vascular bed and their activation causes vasoconstriction with a consequent reduction in carotid blood flow. Compounds which have "5-$HT_1$-like" agonist activity are therefore useful in the treatment of medical conditions which are thought to result from excessive dilation of the carotid bed, such as migraine, cluster headache, chronic paroxysmal hemicrania and headache associated with vascular disorders. Certain compounds of the present invention are also agonists at central 5-$HT_1$ receptors and are therefore useful for the treatment of depression, anxiety, eating disorders, obesity, drug abuse and emesis.

WO-A-92/06973 discloses a series of 3,5-disubstituted indoles having utilities similar to those of the present invention and which are related to compounds of formula (IA), vide infra, but which contain structurally distinct 5-substitutents.

J. Med. Chem., 1963, 6, 719 relates, inter alia, to the synthesis, and antiserotonin and hypotensive properties, of certain 5-acyltryptamines, whilst J. Med. Chem., 1979, 22, 428 reports the serotonin receptor binding affinities of various tryptamine analogues. In addition, the effects of some tryptamine analogues on brain monoamines are described in Neuropharmacology, 1972, 11, 373 (Chem. Abs., 1972, 77, 83394v).

The present invention provides compounds of formula:

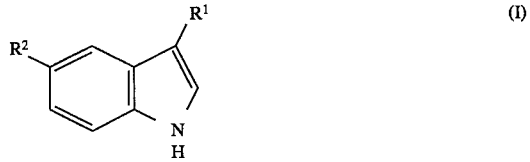

pharmaceutically acceptable salts thereof, and pharmaceutically acceptable solvates (including hydrates) of either entity, wherein $R^1$ is

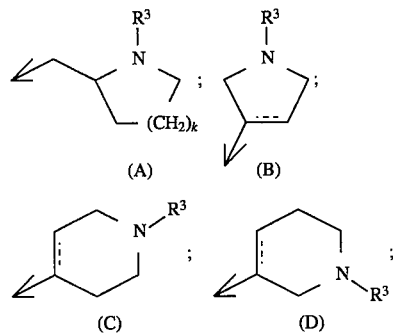

or $CH_2CH_2NR^3R^4$ (E);

$R^2$ is $R^5R^6C(OH)A$ or $R^7COA$;

$R^3$ is H; $C_1$-$C_6$ alkyl; ($R^8CO$) $C_1$-$C_3$ alkylene; ($R^9O_2C$) $C_1$-$C_3$ alkylene; ($R^{10}R^{11}NOC$) $C_1$-$C_6$ alkylene; ($R^{10}R^{11}NO_2S$) $C_1$-$C_3$ alkylene; [$R^8S(O)_m$]$C_1$-$C_3$ alkylene; ($R^{12}O$) $C_2$-$C_4$ alkylene; ($R^{13}NH$) $C_2$-$C_4$ alkylene; ($C_3$-$C_7$ cycloalkyl) $C_1$-$C_3$ alkylene; (aryl) $C_1$-$C_3$ alkylene; (heteroaryl) $C_1$-$C_3$ alkylene; $C_3$-$C_7$ cycloalkyl optionally substituted with HO; $C_3$-$C_6$ alkenyl optionally substituted with aryl; $C_5$-$C_7$ cycloalkenyl; or $C_3$-$C_6$ alkynyl;

$R^4$ is H or $C_1$-$C_6$ alkyl;

$R^5$ and $R^6$ are each independently selected from H; $C_1$-$C_6$ alkyl; $C_1$-$C_4$ perfluoroalkyl; and $C_3$-$C_7$ cycloalkyl; or, together with the carbon atom to which they are attached, form a 3- to 7-membered carbocyclic ring which optionally incorporates a double bond or a heteroatom linkage selected from O, $S(O)_m$, NH, $N(C_1$-$C_4$ alkyl), and $N(C_1$-$C_5$ alkanoyl);

$R^7$ and $R^8$ are each independently selected from $C_1$-$C_6$ alkyl; ($C_3$-$C_7$ cycloalkyl) $C_1$-$C_3$ alkylene; (aryl) $C_1$-$C_3$ alkylene; $C_3$-$C_7$ cycloalkyl; and aryl;

$R^9$ is $C_1$-$C_6$ alkyl; ($C_3$-$C_7$ cycloalkyl) $C_1$-$C_3$ alkylene; (aryl) $C_1$-$C_3$ alkylene; or $C_3$-$C_7$ cycloalkyl;

$R^{10}$ and $R^{11}$ are each independently selected from H; $C_1$-$C_6$ alkyl; ($R^{14}R^{15}NOC$) $C_1$-$C_3$ alkylene; ($R^{16}O$) $C_2$-$C_4$ alkylene; ($C_3$-$C_7$ cycloalkyl) $C_1$-$C_3$ alkylene; (aryl) $C_1$-$C_3$ alkylene; and $C_3$-$C_7$ cycloalkyl; or, together with the nitrogen atom to which they are attached, form a 4- to 7-membered heterocyclic ring which optionally incorporates a further heteroatom linkage selected from O, $S(O)_m$, NH, $N(C_1$-$C_4$ alkyl), and $N(C_1$-$C_5$ alkanoyl);

$R^{12}$ is H; $C_1$-$C_6$ alkyl; ($C_3$-$C_7$ cycloalkyl) $C_1$-$C_3$ alkylene; (aryl) $C_1$-$C_3$ alkylene; $C_3$-$C_7$ cycloalkyl; or aryl;

$R^{13}$ is H; $C_1$-$C_5$ alkanoyl; ($C_1$-$C_4$ alkyl)$SO_2$; or $H_2NSO_2$;

$R^{14}$ and $R^{15}$ are each independently selected from or $C_1$-$C_4$ alkyl;

$R^{16}$ is H; $C_1$-$C_4$ alkyl; or benzyl;

A is a direct link; $C_1$-$C_6$ alkylene optionally branched with $C_1$-$C_4$ alkyl; or $C_2$-$C_6$ alkenylene optionally branched with $C_1$-$C_4$ alkyl;

and k and m are each independently selected from 0, 1 and 2;

with the proviso that, for a compound of formula (IE) wherein $R^2$ is $R^7COA$ and A is a direct link, $R^7$ is not (a) methyl, ethyl, phenyl or 4-chlorophenyl when both $R^3$ and $R^4$ are H;

(b) methyl when both $R^3$ and $R^4$ are methyl; or (c) phenyl when both $R^3$ and $R^4$ are ethyl, or when either of $R^3$ and $R^4$ is ethyl or butyl and the other is H.

In the above definition, a broken line indicates an optional carbon-carbon single bond, aryl means phenyl optionally substituted with one to three substituents independently selected from $C_1$-$C_4$ alkyl, $C_1$-$C_4$ alkoxy, halo, $F_3C$, NC, $H_2NOC$, and HO; heteroaryl means pyrrolyl, furyl, thienyl, oxazolyl, thiazolyl, pyridyl, pyrimidinyl or pyrazinyl; and halo means fluoro, chloro, bromo or iodo.

Unless otherwise indicated, alkylene groups having two or more carbon atoms, alkyl and alkoxy groups having three or more carbon atoms, and alkanoyl, alkenyl and alkynyl groups having four or more carbon atoms, may be straight chain or branched chain.

The compounds of formula (I) may contain one or more asymmetric centres and thus can exist as stereoisomers, i.e. as enantiomers or as diastereoisomers. Furthermore, compounds of formula (I) which contain alkenyl groups can exist as cis-stereoisomers or trans-stereoisomers. In each instance, the invention includes both the separated individual stereoisomers as well as mixtures thereof.

The preferred stereisomers are those compounds of formula (IA) which possess the R-configuration at the 2-position of the azetidine, pyrrolidine or piperidine ring, as represented by formula (IA'):

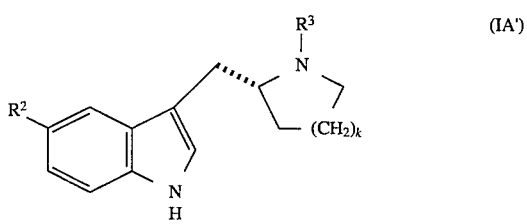

(IA')

Also included in the invention are radiolabelled derivatives of compounds of formula (I) which are suitable for biological studies.

The pharmaceutically acceptable salts of the compounds of formula (I) are, for example, non-toxic acid addition salts formed with inorganic acids such as hydrochloric, hydrobromic, sulphuric and phosphoric acid, with organo-carboxylic acids, or with organo-sulphonic acids. For a review of suitable pharmaceutical salts, see J. Pharm. Sci., 1977, 66, 1–19.

A preferred group of compounds of formula (I) is that consisting of compounds of formula (IA) wherein $R^2$ is $R^5R^6C(OH)A$ or $R^7COA$; $R^3$ is H; $C_1$–$C_4$ alkyl; (benzyl $O_2C$) $C_1$–$C_3$ alkylene; $(R^{10}R^{11}NOC)$ $C_1$–$C_6$ alkylene; $(R^{10}R^{11}NO_2S)$-$C_1$–$C_3$ alkylene; $(R^8SO_2)$ $C_1$–$C_3$ alkylene; $(R^{12}O)$ $C_2$–$C_4$ alkylene; $(R^{13}NH)$ $C_2$–$C_4$ alkylene; $(C_4$–$C_6$ cycloalkyl) $C_1$–$C_3$ alkylene; or (pyridyl) $C_1$–$C_3$ alkylene; $R^5$ and $R^6$ are each independently selected from H; $C_1$–$C_4$ alkyl; $CF_3$; and cyclopentyl; or, together with the carbon atom to which they are attached, form a 4- to 6-membered carbocyclic ring which optionally incorporates an oxygen atom linkage; $R^7$ is $C_1$–$C_4$ alkyl or $C_4$–$C_6$ cycloalkyl; $R^8$ is $C_1$–$C_4$ alkyl; $R^{10}$ and $R^{11}$ are each independently selected from H; $C_1$–$C_4$ alkyl; $(R^{14}R^{15}NOC)$ $C_1$–$C_3$ alkylene; and $(R^{16}O)$-$C_2$–$C_4$ alkylene; or, together with the nitrogen atom to which they are attached, form a 5- to 6-membered heterocyclic ring which optionally incorporates an oxygen atom linkage; $R^{12}$ is H; $C_1$–$C_4$ alkyl; or benzyl; A is a direct link; $C_1$–$C_4$ alkylene; or $C_2$–$C_4$ alkenylene; k is 1; and $R^{13}$, $R^{14}$, $R^{15}$ and $R^{16}$ are as previously defined for formula (IA); compounds of formula (IB) wherein $R^2$ is $R^5R^6C(OH)A$; $R^3$ is H or benzyl; $R^5$ and $R^6$ together with the carbon atom to which they are attached form a 4- to 6-membered carbocyclic ring; A is ethylene or vinyl; and the broken line is absent; compounds of formula (IC) wherein $R^2$ is $R^5R^6C(OH)A$ or $R^7COA$; $R^3$ is H, $C_1$–$C_4$ alkyl or benzyl; $R^5$ and $R^6$ are each independently selected from H and $C_1$–$C_4$ alkyl; or, together with the carbon atom to which they are attached, form a 4- to 6-membered carbocyclic ring; $R^7$ is $C_1$–$C_4$ alkyl; A is a direct link; ethylene or vinyl; and the broken line indicates an optional carbon-carbon single bond; and compounds of formula (IE) wherein $R^2$ is $R_5R^6C(OH)A$; $R^3$ and $R^4$ are each independently selected from H, $C_1$–$C_4$ alkyl and benzyl; $R^5$ and $R^6$ are each $C_1$–$C_4$ alkyl or, together with the carbon atom to which they are attached, form a 4- to 6-membered carbocyclic ring; and A is ethylene or vinyl.

A more preferred group of compounds of formula (I) is that consisting of compounds of formula (IA) wherein $R^2$ is $R^5R^6C(OH)A$ or $R^7COA$; $R^3$ is H; $C_1$–$C_3$ alkyl; $(R^{10}R^{11}NOC)$ $C_1$–$C_5$ alkylene; $CH_3NHO_2SCH_2CH_2$; $CH_3OCH_2CH_2$; or (cyclopropyl) $CH_2$; $R^5$ is methyl, $R^6$ is H methyl, ethyl or $CF_3$, or $R^5$ and $R^6$ together with the carbon atom to which they are attached, form a cyclobutyl, cyclopentyl or 3-tetrahydrofuranyl ring; $R^7$ is methyl; $R^{10}$ and $R^{11}$ are each independently selected from H; methyl; $(CH_3)_2NOCC_2$; $(CH_3)_2NOCCH_2CH_2$; $HOCH_2CH_2$; and $CH_3OCH_2CH_2$; and A is ethylene, propylene or vinyl; compounds of formula (IC) wherein $R^2$ is $R^5R^6C(OH)A$; $R^3$ is H or methyl; $R^5$ is methyl, $R^6$ is H or methyl, or $R^5$ and $R^6$ together with the carbon atom to which they are attached form a cyclopentyl ring; A is ethylene or vinyl; and the broken line indicates an optional carbon-carbon single bond; and a compound of formula (IE) wherein $R^2$ is $R^5R^6C(OH)CH_2CH_2$; $R^3$ is methyl; $R^4$ is H; and $R^5$ and $R^6$ together with the carbon atom to which they are attached form a cyclopentyl ring.

A particularly preferred group of compounds of formula (I) is that consisting of compounds of formula (IA) wherein $R^2$ is $R^5R^6C(OH)A$; $R^3$ is H; methyl; 2-propyl; $CH_2NHOCCH_2CH_2$; $(CH_3)_2NOCCH_2CH_2$; $CH_3NHOCCH_2CH_2$; $CH_3NHOCCH_2CH_2CH_2$; $CH_3NHOCCH_2CH_2CH_2CH_2$; $HOCH_2CH_2NOCCH_2CH_2$; $CH_3OCH_2CH_2$; or (cyclopropyl) $CH_2$; $R^5$ is methyl, $R^6$ is H methyl or $CF_3$, or $R^5$ and $R^6$ together with the carbon atom to which they are attached form a cyclobutyl or cyclopentyl ring; and A is ethylene or vinyl; and a compound of formula (IC) wherein $R^2$ is $CH_3CH(OH)CH_2CH_2$; $R^3$ is methyl; and the broken line is absent.

Especially preferred individual compounds of the invention include:

5-(3-hydroxy-1-butyl)-3-(N-methyl-2(R)-pyrrolidinylmethyl)-1H-indole;

3-(N-cyclopropylmethyl-2(R)-pyrrolidinylmethyl)-5-(3-hydroxy-3-methyl-1-butyl)-1H-indole;

5-[2-(1-hydroxycyclopentyl)ethyl]-3-(2(R)-pyrrolidinylmethyl)-1H-indole;

5-[2-(1-hydroxycyolopentyl)ethyl]-3-(N-methyl-2(R)-pyrrolidinylmethyl)-1H-indole;

5-[2-(1-hydroxycyclopentyl)ethyl]-3-{N-[2-(N-methylcarbamoyl)ethyl]2(R)-pyrrolidinylmethyl}-1H-indole;

and 5-[2-(1-hydroxycyclopentyl)ethyl]-3-{N-[2-(N,N-dimethylcarbamoyl)ethyl]-2(R)-pyrrolidinylmethyl}-1H-indole;

and pharmaceutically acceptable salts thereof, and pharmaceutically acceptable solyates (including hydrates) of either entity.

In another aspect, the present invention provides processes for the preparation of compounds of formula (I), their pharmaceutically acceptable salts, and pharmaceutically acceptable solyates (including hydrates) of either entity, as illustrated below. It will be appreciated by persons skilled in the art that, within the various processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps. It will also be appreciated that various standard functional group interconversions and transformations within certain compounds of formula (I) will provide other compounds of formula (I); examples are ketones to secondary alcohols and vice versa, and alkenes to alkanes, respectively.

(A1)

A compound of formula (IA) wherein $R^3$ is not H may be obtained by selective N-alkylation of the saturated heterocyclic ring of a compound of formula (IA) wherein $R^3$ is H, i.e. a compound of formula (IIA):

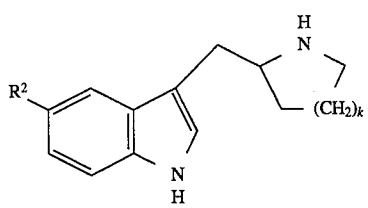

wherein $R^2$ is as previously defined for formula (I) and k is as previously defined for formula (IA), using one or more of the following methods.

1. By reaction of a compound of formula (IIA) with a compound of formula $R^3X$, wherein $R^3$ is as defined for formula (I) or is a conventionally protected precursor thereof (e.g. containing —$NH_2$ protected as phthalimido), and X is a suitable leaving group, e.g. halo (preferably chloro, bromo or iodo), $C_1$–$C_4$ alkanesulphonyloxy, trifluoromethanesulphonyloxy or arylsulphonyloxy (preferably benzenesulphonyloxy or p-toluenesulphonyloxy), in the presence of an appropriate base, e.g. sodium or potassium carbonate or bicarbonate, Or triethylamine, in a suitable solvent such as a $C_1$–$C_4$ alkanol, 1,2-dimethoxyethane, acetenitrile, dimethylformamide or N,N-dimethylacetamide, and optionally in the presence of sodium or potassium iodide. The reaction can be conducted at from about 0° C. to about 150° C., preferably at from room temperature to 100° C., and, where appropriate, is followed by a standard deprotection step.

2. By reductive alkylation of a compound of formula (IIA) using the appropriate aldehyde-, ketone- or carboxylic acid-containing $R^3$ precursor. In the case of an aldehyde or ketone precursor, the substrate (IIA) and carbonyl reagent may be reacted together under conventional catalytic hydrogenation conditions or in the presence of sodium cyanoborohydride, in a suitable solvent such as methanol or ethanol, at about room temperature. Alternatively, the reductive alkylation may be achieved by a two-step procedure in which the intermediate enamine is formed initially, under conventional conditions, and subsequently reduced to the required amine, e.g. using sodium cyanoborohydride in tetrahydrofuranmethanol at about room temperature.

In the case of a carboxylic acid precursor, the substrate (IIA) and the said acid reagent may be reacted together in the presence of excess sodium borohydride in a suitable solvent; preferably the carboxylic acid itself is used as solvent whenever possible. Since this reductive alkylation proceeds via in situ formation of the corresponding sodium triacyloxyborohydride, obvious variations are to employ preformed reagent when commercially available, e.g. sodium triacetoxyborohydride (for N-ethylation), or to preform it in a separate in situ step using the stoichiometric amount of carboxylic acid in a suitable solvent. An example of the latter procedure involves the treatment of six equivalents of the carboxylic acid with two equivalents of sodium borohydride in dry tetrahydrofuran at about room temperature. When formation of the required sodium triacyloxyborohydride is complete, the reaction mixture is treated with a solution of one equivalent of the substrate (IIA) in the same solvent and the subsequent reaction step is conducted at from about room temperature to about 70° C., preferably 50°–55° C.

3. When $R^3$ is $C_2$—$C_4$ alkyl or $C_3$–$C_7$ cycloalkyl, each substituted at the 2-position with a hydroxy group, by reaction of a compound of formula (IIA) with the appropriate epoxide-containing $R^3$ precursor, optionally in the presence of a tertiary amine base, e.g. triethylamine, and preferably in a suitable solvent such as a $C_1$–$C_4$ alkanol or 1,2-dimethoxyethane. The reaction can be conducted at from about 0° C. to about 150° C., preferably at from room temperature to 60° C. using methanol as solvent.

When $R^3$ is 2-hydroxyethyl, an "ethylene oxide equivalent" is preferably employed. Thus a compound of formula (IIA) may be reacted with ethylene carbonate in a suitable solvent such as dimethylformamide at about 120° C.

4. When $R^3$ is either $C_2$–$C_3$ alkyl substituted at the 2-position with an electron withdrawing group such as $R^8CO$, $R^9O_2C$, $R^{10}R^{11}NOC$, $R^{10}R^{11}NO_2S$, $R^8SO$, $R^8SO_2$, or certain aryl or heteroaryl systems (e.g. 2- or 4-pyridyl), or also $C_4$–$C_6$ alkyl substituted at the 2-position with $R^{10}R^{11}NOC$, by conjugate addition (Michael-type reaction) of a compound of formula (IIA) to the corresponding α, β-unsaturated ketone-, ester-, amide-, sulphonamide-, sulphoxide-, sulphone-, arene- or heteroarene-containing $R^3$ precursor respectively, wherein $R^8$, $R^9$, $R^{10}$ and $R^{11}$ are as defined for formula (I), optionally in the presence of a tertiary amine base such as triethylamine. The reaction may optionally be conducted in a suitable solvent, e.g. 1,2-dimethoxyethane or N,N-dimethylacetamide, at from about 0° C. to about 100° C., preferably at about 85° C. or about 100° C. respectively. Alternatively, the reaction may be effected in pyridine, which serves both as tertiary amine base and as solvent, preferably at about 115° C.

A compound of formula (IIA) may be obtained from a compound of formula (IIIA):

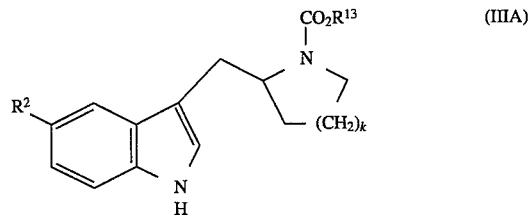

wherein $R^2$ and k are as previously defined for formula (IIA) and $R^{13}$ forms part of a conventional amino acid N-protecting group, i.e. a carbamate, wherein $R^{13}$ is preferably benzyl or t-butyl. N-Deprotection of a compound of formula (IIIA) can be achieved using standard methodology; for example, when $R^{13}$ is benzyl, by palladium-catalysed hydrogenolysis and, when $R^{13}$ is t-butyl, by protonolysis using trifluoroacetic acid or hydrogen chloride.

Alternatively, when $R^{13}$ is benzyl, N-deprotection can be effected by modification of the procedure reported in Tetrahedron Letters, 1988, 29, 2983, in which (IIIA) is treated with an excess of a tri(lower alkyl)silane in the presence of a palladium(II) salt and an excess of a tri(lower alkyl)amine in a suitable solvent such as a $C_1$–$C_4$ alkanol. Preferably the reaction is conducted using triethylsilane, palladium(II) acetate and triethylamine in ethanol at about room temperature.

Depending on the nature of $R^2$, a compound of formula (IIIA) can be obtained by a variety of synthetic methods.

For example, when A is $C_2$–$C_6$ alkylene, by reduction of a compound of formula (IVA):

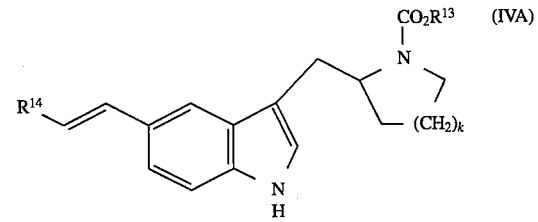

wherein $R^{14}$ is $R^5R^6C(OH)(CH_2)_n$ or $R^7CO(CH_2)_n$ wherein n is 0, 1, 2, 3 or 4 and $R^5$, $R^6$ and $R^7$ are as previously defined for formula (I), and $R^{13}$ and k are as previously defined for formula (IIIA). This may be achieved by conventional catalytic or catalytic transfer hydrogenation, preferably using palladium as catalyst and, in the latter process, ammonium formate as the hydrogen source. Alternatively, the trialkylsilane/palladium(II) salt procedure described above may be employed.

Clearly, when $R^{13}$ is benzyl, a compound of formula (IVA) may be converted directly to a compound of formula (IIA) wherein $R^2$ is $CH_2CH_2R^{14}$ under these conditions.

Alternatively, when $R^{13}$ is t-butyl, N-deprotection of a compound of formula (IVA) by the protonolysis conditions previously mentioned may provide a compound of formula (IIA) wherein $R^2$ is $CH=CHR^{14}$, i.e. wherein A is $C_2$–$C_6$ alkenylene.

A compound of formula (IVA) may be obtained from a compound of formula (VA):

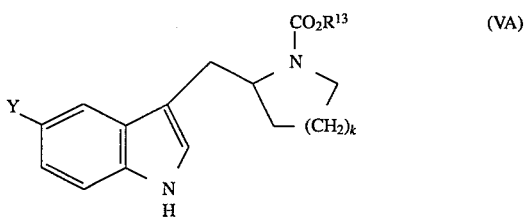

wherein Y is chloro, bromo or iodo (preferably bromo), and $R^{13}$ and k are as previously defined for formula (IVA), with an alkene of formula $CH_2=CHR^{14}$, wherein $R^{14}$ is as previously defined for formula (IVA), using the Heck reaction. Thus the desired coupling is achieved using, for example, an excess of the required alkene, in the presence of palladium(II) acetate, tri-o-tolylphosphine and triethylamine, in a suitable solvent such as acetonitrile or dimethylformamide, at from about 80° C. to about 160° C.

A compound of formula (VA) may be obtained from a compound of formula (VIA):

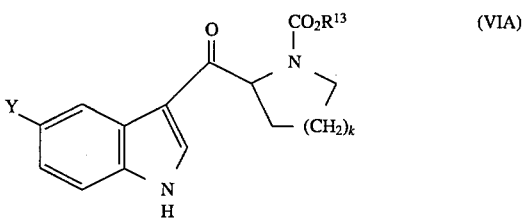

wherein $R^{13}$, k and Y are as previously defined for formula (VA), by selective and exhaustive reduction of the ketonic carbonyl group. This may be achieved using an alkali metal borohydride salt, preferably lithium borohydride, in a suitable solvent such as tetrahydrofuran, at from about room temperature to about 70° C.

A compound of formula (VIA) may be obtained as described in WO-A-9206973.

(A2)

An alternative approach to a compound of formula (IA), wherein in $R^2$ A is $C_2$–$C_6$ alkylene, involves the reaction of a compound of formula (VIIA):

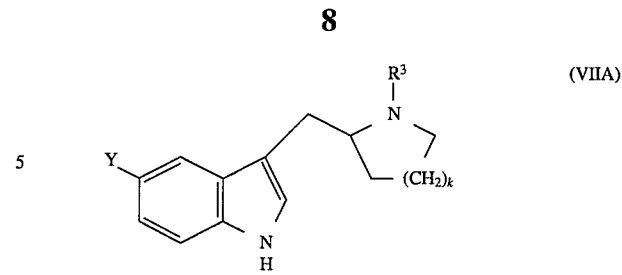

wherein $R^3$ is as previously defined for formula (I) and k and Y are as previously defined for formula (VIA), with an alkene of formula $CH_2=CHR^{14}$ wherein $R^{14}$ is as previously defined, under the Heck reaction conditions previously described for the conversion of (VA) to (IVA), followed by reduction of the resulting alkene as already described for the reduction of (IVA) to (IIIA).

A compound of formula (VIIA) wherein $R^3$ is not H may be obtained by selective N-alkylation of a compound of formula (VIIIA):

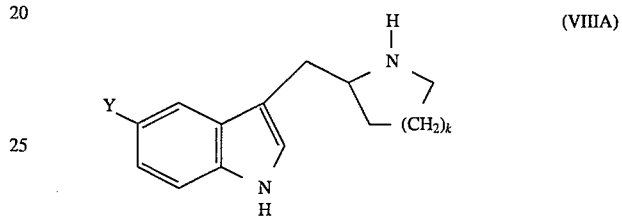

wherein k and Y are as previously defined for formula (VIIA), by analogy with the procedures described earlier for the conversion of (IIA) to (IA).

When, specifically, $R^3$ is methyl, the said compound of formula (VIIA) may be obtained from a compound of formula (VA) wherein $R^{13}$ is benzyl, and k and Y are as previously defined for formula (VA), by reduction with lithium aluminium hydride, as described in WO-A-9206973 for the case wherein Y is bromo.

A compound of formula (VIIIA) may be obtained from a compound of formula (VA) wherein $R^{13}$, k and Y are as previously defined for formula (VA) by the standard N-deprotection methodology already described. Preferably however, when $R^{13}$ is benzyl, deprotection is effected by a non-hydrogenolytic procedure such as protonolysis in a suitable solvent using, for example, hydrogen bromide in glacial acetic acid or hydrogen chloride in methanol, at about room temperature, a Lewis acid-catalysed nucleophilic deprotection using, for example, boron trifluoride etherate and excess ethanethiol in a suitable solvent such as dichloromethane at about room temperature, or an alkaline deprotection using, for example, potassium hydroxide in a suitable solvent such as a $C_1$–$C_4$ alkanol, preferably n-butanol.

(A3)

Certain compounds of formula (IA) wherein $R^2$ is $R^7COA$, wherein $R^7$ is as previously defined for formula (I) but is not aryl and A is a direct link, may be obtained by analogy with the processes described previously under (A1) and (A2) wherein the compound of formula (VA) or (VIIA) is coupled under Heck reaction conditions with an enol ether of formula (IXA):

wherein $R^{15}$ and $R^{16}$ are both H, or one of $R^{15}$ and $R^{16}$ is H and the other is $C_1$–$C_5$ alkyl, ($C_3$–$C_7$ cycloalkyl) $C_1$–$C_2$ alkylene or (aryl) $C_1$–$C_2$ alkylene, or $R^{15}$ and $R^{16}$ together with the carbon atom to which they are attached form $C_3$-$C_7$ cycloalkyl, and $R^{17}$ is $C_1$-$C_4$ alkyl, followed by acid-catalysed hydrolysis of the intermediate, coupled enol ether. Because of the commercial availability of vinyl ethers, i.e. compounds of formula (IXA) wherein $R^{15}$ and $R^{16}$ are both H, this is a particularly convenient method for introducing an acetyl group into the 5-position of a compound of formula (VA) or (VIIA).

(A4)

A compound of formula (IA) wherein $R^2$ is $R^5R^6C(OH)A$, wherein $R^5$ and $R^6$ are as previously defined for formula (I) and A is a direct link, may also be obtained by analogy with the processes described under (A1) and (A2) wherein the 5-substituent is introduced into a compound of formula (VA) or (VIIA) by coupling a 5-organometallic substituted derivative thereof, e.g. an aryllithium or Grignard reagent, with the appropriate aldehyde or ketone of formula $R^5R^6C=O$ wherein $R^5$ and $R^6$ are as defined above.

For example, (VA) or (VIIA) is treated with the required excess of a solution of t-butyllithium in hexane in a suitable anhydrous solvent, such as dry tetrahydrofuran, at from about $-50°$ C. to about $-70°$ C.; if required, the temperature may be allowed to rise to about room temperature to ensure complete formation of the desired 5-lithium derivative. Generally, the reaction mixture is again cooled to about $-70°$ C. before addition of the appropriate aldehyde or ketone and subsequent quenching.

Variations include the sequential use of potassium hydride and t-butyllithium or prior protection of the indole 1-position, e.g. with a triisopropylsilyl group, followed by treatment with n-butyllithium, to generate the desired 5-lithium derivative.

(A5)

A compound of formula (IA) wherein $R^2$ is $R^7COA$, wherein $R^7$ is as previously defined for formula (I) and A is a direct link, may also be obtained from a compound of formula (VA) or (VIIA) via the organometallic derivatives identified in (A4) above by reaction with the appropriate electrophilic acylation reagent, e.g. ester or nitrile (followed in the latter case by hydrolysis of the intermediate imine salt).

(A6).

As previously suggested, certain compounds of formula (IA) can be prepared from other compounds of formula (IA) by, for example, the following conventional functional group interconversions and transformations:

(a) a compound of formula (IA) wherein $R^2$ contains a secondary alcohol group is obtainable from the corresponding ketone of formula (IA) by reduction. The choice of appropriate reducing agent will be dependent, inter alia, on the nature of $R^3$ but will include aluminium hydride and borohydride salts. Preferably the reaction is conducted using sodium borohydride in a suitable solvent such as a $C_1$-$C_4$ alkanol, preferably ethanol, at about room temperature.

The reverse interconversion also forms part of the invention and the relevant criteria for selection of an appropriate oxidising reagent will be evident to persons skilled in the art. A preferred procedure is the use of activated manganese dioxide in a suitable solvent such as an acetonitrile-dichloromethane mixture at about room temperature;

(b) a compound of formula (IA) wherein $R^2$ contains a tertiary alcohol group is obtainable from the corresponding ketone of formula (IA) by reaction with the required excess of a conventional organometallic reagent such as an alkyl- or cycloalkyl-lithium or Grignard reagent;

(c) a compound of formula (IA) wherein in $R^2$ A is $C_2$-$C_6$ alkylene is obtainable from the corresponding compound of formula (IA) wherein A is $C_2$-$C_6$ alkenylene by a variety of alkene reduction procedures already described;

(d) a compound of formula (IA) wherein $R^3$ contains a $R^{10}R^{11}NOC$ substituent is obtainable from a corresponding ester of formula (IA), i.e. wherein $R^3$ contains a $R^9O_2C$ substituent, by direct amination using an amine of formula $R^{10}R^{11}NH$. The reaction is preferably carried out using an excess of the amine in a suitable solvent such as a $C_1$-$C_4$ alkanol at an elevated temperature, e.g. the reflux temperature of the reaction medium. For low boiling amines, the reaction is preferably conducted in a sealed vessel.

The same over-all transformation can be effected indirectly via the intermediacy of the corresponding carboxylic acid, i.e. a compound of formula (IA) wherein $R^3$ contains a $HO_2C$ substituent. Depending on the nature of the ester, its deprotection may be achieved by acid or alkaline hydrolysis, protonolysis (e.g. when $R^9$ is t-butyl) or hydrogenolysis (e.g. when $R^9$ is benzyl). Conversion of the acid to the required amide may also be achieved by a variety of methods. For example, the acid may be activated by formation of the corresponding acyl halide, e.g. bromide or chloride, followed by reaction of the latter with an amine of formula $R^{10}R^{11}NH$ optionally in the presence of a reaction-inert base to act as acid scavenger. Preferably, any of a host of standard amide bond-forming (peptide coupling) reagents may be used. For example, the acid may be activated using a carbodiimide such as 1-ethyl-3-dimethylaminopropylcarbodiimide, optionally in the presence of 1-hydroxybenzotriazole and a reaction-inert amine such as N-methylmorpholine, followed by in situ reaction of the activated acid with an amine of formula $R^{10}R^{11}NH$;

(e) a compound of formula (IA) wherein $R^3$ contains a $R^8SO$ or a $R^8SO_2$ substituent is obtainable from the corresponding sulphide of formula (IA), i.e. wherein $R^3$ contains a $R^8S$ substituent, either by controlled oxidation using a stoichiometric amount of oxidising agent, or by using the required excess of oxidising agent, respectively. Suitable oxidising agents are, for example, a peracid such as metachloroperbenzoic acid, hydrogen peroxide or nitronium tetrafluoroborate.

(B)

A compound of formula (IB) may, in general terms, be obtained by analogy with the processes (A1)–(A6) already described above for the preparation of compounds of formula (IA).

For example, comparably with process (A1), a compound of formula (IB) wherein $R^3$ is not H may be obtained from a compound of formula (IB) wherein $R^3$ is H, i.e. a compound of formula (IIB):

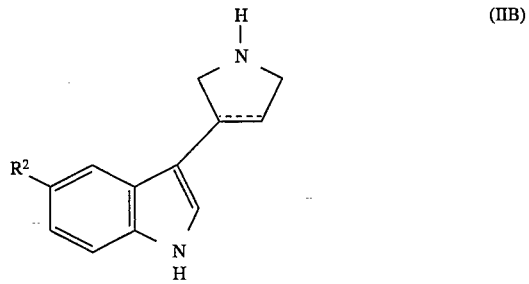

wherein $R^2$ is as previously defined for formula (I) and the broken line is as previously defined for formula (IB), by analogy with the methods already described for the conversion of a compound of formula (IIA) to a compound of formula (IA).

Certain compounds of formula (IIB) wherein both $R^2$ and the heterocyclic 3-substituent contain fully saturated carbon-carbon. bonds may be conveniently obtained from a compound of formula (IIIB):

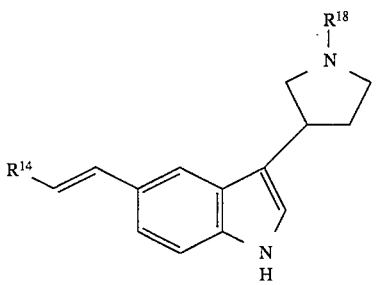
(IIIB)

wherein $R^{18}$ is a protecting group which is removable under the conventional catalytic hydrogenation conditions previously described for the conversion of (IVA) to (IIIA), and $R^{14}$ is as previously defined for formula (IVA). Preferably $R^{18}$ is benzyl.

A compound of formula (IIIB) may be obtained from a compound of formula (IVB):

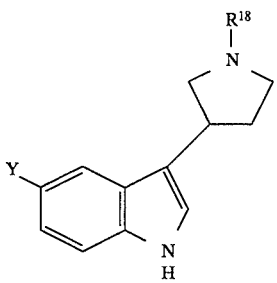
(IVB)

wherein Y is as previously defined for formula (VA) and $R^{18}$ is as previously defined for formula (IIIB), by analogy with the Heck reaction procedure already described for the conversion of (VA) to (IVA).

A compound of formula (IVB) may be obtained by reduction of a compound of formula (VB):

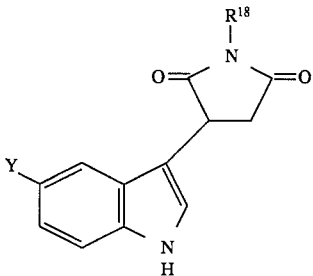
(VB)

wherein Y and $R^{18}$ are as previously defined for formula (IVB). This may be achieved, for example, using lithium aluminium hydride in a suitable solvent such as tetrahydrofuran at from about room temperature to about 70° C., preferably at 65° to 70° C.

A compound of formula (VB) may be obtained by coupling a compound of formula (VIB):

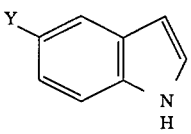
(VIB)

wherein Y is as previously defined for formula (VB), with a compound of formula (VIIB):

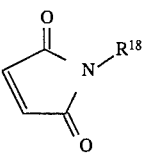
(VIIB)

wherein $R^{18}$ is as defined for formula (VB), in a suitable solvent such as glacial acetic acid preferably at about 115°–120° C.

Clearly, by analogy with process (A2), when $R^{18}$ is a value of $R^3$ as previously defined for formula (IB), certain compounds of formula (IB) may be obtained directly from a compound of formula (IVB) using the Heck reaction step previously described, optionally followed by further transformations of the $R^2$ substituent (vide supra). Such compounds of formula (IVB) may also be used in processes analogous to (A3), (A4) and (A5).

Most directly, however, certain compounds of formula (IB) may be obtained from a compound of formula (I) wherein $R^1$ is H and $R^2$ is as previously defined for formula (I), obtainable from a compound of formula (VIB) by previously described methodology, by coupling with a compound of formula (VIIB) wherein $R^{18}$ is a value of $R^3$ as previously defined for formula (IB).

(C)

A compound of formula (IC) may also, in general terms, be obtained by analogy with process (A1)–(A6).

For example, comparably with process (A1), a compound of formula (IC) wherein $R^3$ is not H may be obtained from a compound of formula (IC) wherein $R^3$ is H, i.e. a compound of formula (IIC):

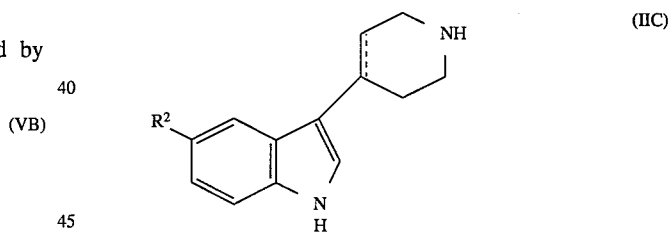
(IIC)

wherein $R^2$ is as previously defined for formula (I) and the broken line is as previously defined for formula (IC), by analogy with the methods already described for the conversion of (IIA) to (IA).

A compound of formula (IIC) may be obtained from a compound of formula (IIIC):

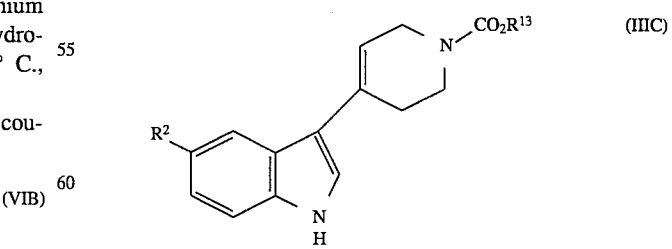
(IIIC)

wherein $R^{13}$ is as previously defined for formula (IIIA) and $R^2$ is as previously defined for formula (IIC), by analogy with the methods already described for the conversion of (IIIA) to (IIA).

Certain compounds of formula (IIIC) may be obtained from a compound of formula (IVC):

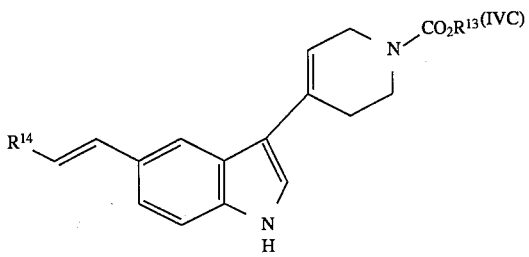

wherein $R^{14}$ is as previously defined for formula (IVA) and $R^{13}$ is as previously defined for formula (IIIC), by analogy with the methods already described for the conversion of (IVA) to (IIIA).

A compound of formula (IVC) may be obtained from a compound of formula (VC):

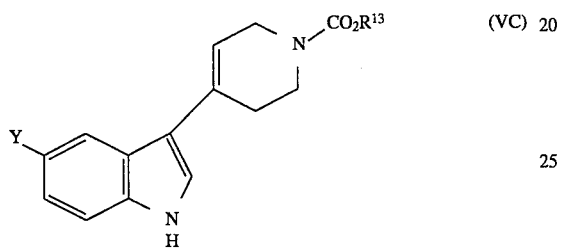

wherein Y is as previously defined for formula (VA) and $R^{13}$ is as previously defined for formula (IVC), by analogy with the Heck. reaction procedure already described for the conversion of (VA) to (IVA).

A compound of formula (VC) may be obtained by reaction of a compound of formula (VIB) with a compound of formula (VIC):

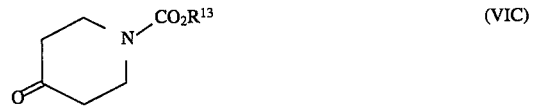

wherein $R^{13}$ is as previously defined for formula (VC), in the presence of a base, e.g. potassium hydroxide, in a suitable solvent such as a $C_1$–$C_3$ alkanol, preferably methanol, at about the reflux temperature of the reaction medium. Alternative reaction conditions are described in EP-A-0303507.

Again, several variations of the above process are possible. For example, when certain compounds of formula (VIIC):

wherein $R^3$ is as previously defined for formula (IC), are readily accessible, the said compounds may be condensed directly with either a compound of formula (VIB) or a compound of formula (VIIIC):

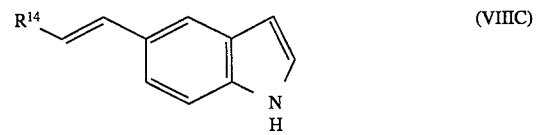

wherein $R^{14}$ is as previously defined for formula (IVC). A compound of formula (VIIIC) may be obtained from a compound of formula (VIB) using the Heck procedure previously described for the conversion of (VA) to (IVA).

Clearly, and most directly, said compounds of formula (VIIC) may be condensed with a compound of formula (I), wherein $R^1$ is H and $R^2$ is as previously defined for formula (I), which in turn is obtainable from a compound of formula (VIB) by previously described methodology.

By analogy with process (A2), the condensation product of (VIIC) and (VIB) is then subjected to the above Heck procedure. Alternatively, it may be used in processes analogous to (A3), (A4) and (A5).

More specifically, when $R^3$ is benzyl, i.e. when N-benzyl-4-piperidone is used as starting material, this will provide an alternative route to a compound of formula (IIC) wherein the broken line represents no bond.

(D)

A compound of formula (ID) is obtainable by analogy with the processes described in (C) for the preparation of compounds of formula (IC).

For example, a compound of formula (ID) wherein $R^3$ is not H may be obtained from a compound of formula (ID) wherein $R^3$ is H, i.e. a compound of formula (IID):

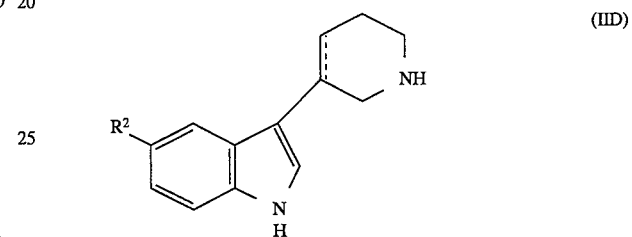

wherein $R^2$ is as previously defined for formula (I) and the broken line is as previously defined for formula (ID), by analogy with the methods already described for the conversion of (IIA) to (IA).

A compound of formula (IID) may be obtained by analogy with the process steps described above for the preparation of a compound of formula (IIC), using the 3-piperidone analogues of (VIC) and (VIIC).

(E)

Using an approach similar to that of process (A1), a compound of formula (IE) may be obtained from a compound of formula (IIE):

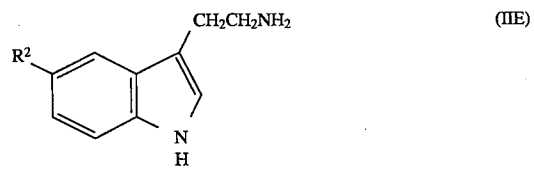

wherein $R^2$ is as previously defined for formula (I), by analogy with the methods already described for the conversion of (IIA) to (IA). However, when $R^3$ and $R^4$ are different but are not H, or when only one of $R^3$ and $R^4$ is H, it may be advantageous to employ an amine-protecting group strategy in order to obviate dialkylation of the primary amino group; examples of conventional amine-protecting groups are benzyl, trifluoroacetyl, t-butoxycarbonyl, benzyloxycarbonyl and 2,2,2-trichloroethoxycarbonyl. The person skilled in the art will recognise the most suitable protecting group required when consideration.is given, inter alia, to the alkylating reagents to be used and the functional groups present in the starting material and product; such a person will also recognise when conventional protection of the indole 1-position is beneficial. When $R^3$ and $R^4$ are identical but are not H, the required compound of formula (IE) may be conveniently obtainable in a one-pot reaction without the need for primary amine protection.

Certain compounds of formula (IIE), namely those which do not contain a ketone group (unless appropriately protected) within the R² substituent, may be obtained from a compound of formula (IIIE):

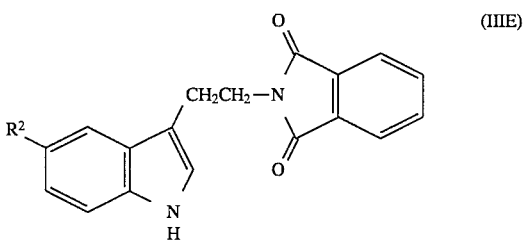

wherein R² is as previously defined for formula (IIE), by deprotection of the amino group. This is achievable, for example, by treating the phthalimide derivative with an excess of hydrazine hydrate in a $C_1$–$C_4$ alkanol, preferably ethanol, as solvent at from about room temperature to about the reflux temperature of the reaction medium, preferably at 75°–80° C.

Certain compounds of formula (IIIE) may be obtained from a compound of formula (IVE):

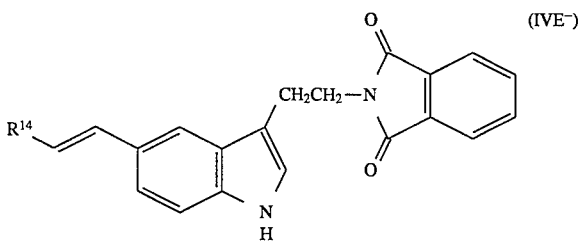

wherein $R^{14}$ is as previously defined for formula (IVA), by analogy with the methods already described for the conversion of (IVA) to (IIIA).

A compound of formula (IRE) may be obtained from a compound of formula (VE):

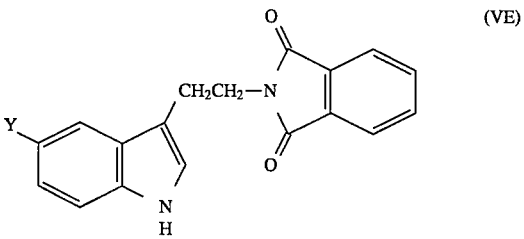

wherein Y is as previously defined for formula (VA), by analogy with the Heck reaction procedure already described for the conversion of (VA) to (IVA).

A compound of formula (VE) may be obtained using standard Fischer indole synthesis methodology in which, for example, the appropriate 4-halophenylhydrazine hydrochloride salt is reacted with 4-phthalimido-n-butyraldehyde diethyl acetal, as described in U.S. Pat. No. 4,252,803 for the corresponding 5-bromo analogue.

In an alternative process, analogous to process (A2), a compound of formula (IE) may be obtained directly from a compound of formula (VIE):

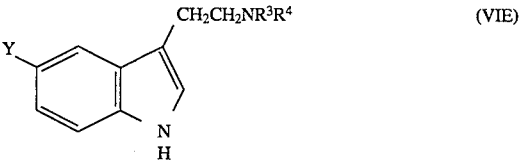

wherein R³ and R⁴ are as previously defined for formula (IE) and Y is as previously defined for formula (VE), by analogy with the Neck reaction procedure mentioned above for the conversion of (VA) to (IVA).

The indoles of formula (VIE) may also be obtained using the Fischer indole reaction, examples of which are illustrated in U.S. Pat. No. 4,252,803.

A further convenient process for the preparation of certain compounds of formula (IE) via a compound of formula (VIE) involves the reaction of a compound of formula (VIB) with oxalyl chloride in a suitable solvent such as anhydrous tetrahydrofuran at from about 0° C. to about 30° C., preferably at about room temperature, followed by in situ treatment of the intermediate acyl chloride with an amine of formula $R^3R^4NH$, wherein R³ and R⁴ are as previously defined for formula (IE), at from about 0° C. to about room temperature, preferably at about 0° C. Next, the resulting amide is exhaustively reduced to a compound of formula (VIE) using a powerful reducing agent such as lithium aluminium hydride in a suitable solvent such as anhydrous tetrahydrofuran at from about room temperature to about 70° C., preferably at 65° to 70° C.

Clearly, if R³ is benzyl and is removed during the further processing of (VIE) to a compound of formula (IE), then further elaboration of the terminal secondary amine group, as previously described, will provide further compounds of formula (IE).

Further variants include the use of a compound of formula (VIE) in process analogous to (A3), (A4) and (A5), and also processes analogous to those described in (A6).

Compounds of formula $CH_2=CHR^{14}$ wherein $R^{14}$ is as previously defined for formula (IVA), those of formulae (IXA), (VIB) and (VIIB), and also those of formulae (VIC) and (VIIC) together with the corresponding 3-piperidones, and the various reagents required for the processes hereinbefore disclosed, when neither commercially available nor subsequently described, can be obtained either by analogy with the reactions described in the Examples and Preparations sections or by conventional synthetic procedures, in accordance with standard textbooks on organic chemistry or literature precedent, from readily accessible starting materials using appropriate reagents and reaction conditions. Clearly, when the preferred stereoisomers of formula (IA') are required, the compounds of formulae (VIA) will possess the 2R-configuration.

Persons skilled in the art will recognise that the alkenes depicted hereinbefore may be obtained in cis- or trans-stereoisomeric forms, or as mixtures of cis- and trans-stereoisomers, and are represented in one such form only in the interests of clarity and convenience. Such persons will also be aware of variations of, and alternatives to, those reactions described hereinafter for the preparation of compounds of formula (I).

The pharmaceutically acceptable acid addition salts of compounds of formula (I) may also be prepared in a conventional manner. For example a solution of the free base is treated with the appropriate acid, either neat or in an appropriate solvent, and the resulting salt isolated either by filtration or by evaporation under vacuum of the reaction solvent. Certain such salts may be formed or interconverted using ion-exchange resin techniques.

The compounds of the invention are selective agonists at the "5-HT₁-like" subtype of the 5-HT (serotonin) receptor and are therefore useful in the curative or prophylactic treatment of migraine and associated conditions such as cluster headache, chronic paroxysmal hemicrania and headache associated with vascular disorders. Certain of these compounds are also agonists at central 5-HT₁ receptors and are therefore useful for the treatment of depression, anxiety, eating disorders, obesity, drug abuse and emesis.

The in vitro evaluation of the "5-HT$_1$-like" receptor agonist activity of the compounds of the invention is carried out by testing the extent to which they mimic sumatriptan in contracting the isolated dog saphenous vein strip (P.P.A. Humphrey et al., Brit. J. Pharmacol., 1988, 94, 1123). This effect can be blocked by methiothepin, a known 5-HT antagonist. Sumatriptan is known to be useful in the treatment of migraine and produces a selective increase in carotid vascular resistance in the anaesthetized dog and a consequent decrease in carotid arterial blood flow. It has been suggested (W. Feniuk et al., Brit. J. Pharmacol., 1989, 96, 83) that this is the basis of its efficacy.

The 5-HT$_1$ agonist activity of the compounds of the invention can be measured in in vitro receptor binding assays as described for the 5-HT$_{1A}$ receptor, using rat cortex as the receptor source and [$^3$H]8-OH-DPAT as the radioligand (D. Hoyer et al., Europ. J. Pharmacol., 1985, 118, 13), and as described for the 5-HT$_{1D}$ receptor, using bovine caudate as the receptor source and [$^3$H]5-HT as the radioligand (R. E. Heuring and S. J. Peroutka, J. Neuroscience, 1987, 7, 894).

In therapy, the compounds of formula (I), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example, intravenously, intramuscularly or subcutaneously. For parenteral administration, they are best used in the form of a sterile aqueous solution which may contain other substances, for example, enough salts or glucose to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formula (I), their pharmaceutically acceptable salts, and pharmaceutically acceptable solvates of either entity, will be from 0.1 ng to 20 mg/Kg (in single or divided doses). Thus tablets or capsules will contain from 5 ng to 0.5 g of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are metired, and such within the scope of this invention.

Alternatively, the compounds of formula (I), their pharmaceutically acceptable salts, and pharmaceutically acceptable solvates of either entity, can be administered in the form of a suppository or pessary, or they may be applied topically in the form of a lotion, solution, cream, ointment or dusting powder. For example, they can be incorporated into a cream consisting of an aqueous emulsion or polyethylene glycols or liquid paraffin; or they can be incorporated, at a concentration of from 1 to 10%, into an ointment consisting of a white wax or white soft paraffin base together with such stabilisers and preservatives as may be required.

The compounds of formula (I), their pharmaceutically acceptable salts, and pharmaceutically acceptable solyates of either entity, can also be administered intranasally or by inhalation and are conveniently delivered in the form of a solution or suspension from a pump spray container, which is squeezed or pumped by the patient, or as an aerosol spray presentation from a pressurised container or a nebuliser with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. The pressurised container or nebuliser may contain a solution or suspension of the active compound. Capsules and cartridges (made, for example, from gelatin) for use in an inhaler or insufflator may be formulated containing a powder mix of a compound of the invention and a suitable powder base such as lactose or starch.

Aerosol formulations are preferably arranged so that each metered dose or "puff" of aerosol contains from 1 ng to 1000 μg of a compound of formula (I), or a pharmaceutically acceptable salt thereof, or a pharmaceutically acceptable solvate of either entity, for delivery to the patient. The overall daily dose with an aerosol will be within the range of from 5 ng to 10 mg which may be administered in a single dose or, more usually, in divided doses throughout the day.

Thus the invention provides pharmaceutical compositions comprising a compound of formula (I), or a pharmaceutically acceptable salt thereof, or a pharmaceutically acceptable solrate (including hydrate) of either entity, together with a pharmaceutically acceptable diluent or carrier.

The invention also provides a compound of formula (I), or a pharmaceutically acceptable salt thereof, or a pharmaceutically acceptable solvate (including hydrate) of either entity, or a pharmaceutical composition containing any of the foregoing, for use as a medicament.

The invention further includes the use of a compound of formula (I), or a pharmaceutically acceptable salt thereof, or a pharmaceutically acceptable solvate (including hydrate) of either entity, or a pharmaceutical composition containing any of the foregoing, both for the manufacture of a medicament for the curative or prophylactic treatment of migraine or an associated condition such as cluster headache, chronic paroxysmal hemicrania or headache associated with a vascular disorder, or of depression, anxiety, an eating disorder, obesity, drug abuse or emesis, and also for the manufacture of a medicament for the curative or prophylactic treatment of a medical condition for which a selective agonist of 5-HT$_1$-like receptors is indicated.

In a further aspect, the invention provides both a method of treating a human being to cure or prevent migraine or an associated condition such as cluster headache, chronic paroxysmal hemicrania or headache associated with a vascular disorder, or depression, anxiety, an eating disorder, obesity, drug abuse or emesis, and also a method of treating a human being to cure or prevent a medical condition for which a selective agonist of 5-HT$_1$-like receptors is indicated, which comprises treating said human being with an effective amount of a compound of formula (I), or a pharmaceutically acceptable salt thereof, or a pharmaceutically acceptable solvate (including hydrate) of either entity, or a pharmaceutical composition containing any of the foregoing.

The syntheses of the compounds of the invention and of the intermediates for use therein are illustrated by the following Examples and Preparations. The purity of the compounds was routinely monitored by thin layer chromatography (Rf) using Merck Kieselgel 60 F$_{254}$ plates and the following solvent systems (SS):

1. dichloromethane:methanol:0.880 aqueous ammonia, 93:7:1;

2. dichloromethane:ethanol:0.880 aqueous ammonia, 90:10:1;
3. hexane:ether, 1:1;
4. dichloromethane:ethanol:0.880 aqueous ammonia, 25:8:1;
5. hexane:ethyl acetate, 3:1;
6. ethyl acetate:diethylamine, 95:5;
7. dichloromethane:methanol:0.880 aqueous ammonia, 90:10:1;
8. dichloromethane:methanol, 99:1;
9. dichloromethane:methanol:0.880 aqueous ammonia, 90:10:2;
10. hexane:ethyl acetate, 1:1;
11. dichloromethane:methanol:0.880 aqueous ammonia, 89:10:1;
12. dichlormethane:methanol:0.880 aqueous ammonia, 80:20:2;
13. dichloromethane:methanol:0.880 aqueous ammonia, 90:10:0.5;
14. hexane:ethyl acetate:diethylamine, 70:25:5;
15. dichloromethane:methanol:0.880aqueous ammonia, 86.5:12.5:1;
16. dichloromethane;
17. ethyl acetate;
18. dichloromethane:methanol, 98:2;
19. dichloromethane:ethanol, 95:5;
20. dichloromethane:methanol, 95:5.

$^1$H Nuclear magnetic reasonance (NMR) spectra were recorded using either a Nicolet QE-300 or a Bruker AC-300 spectrometer and were in all cases consistent with the proposed structures. Chemical shifts (δ) are given in parts-per-million downfield from tetramethylsilane using conventional abbreviations for designation of major peaks: s, singlet; d, doublet; dd, doublet of doublets; t, triplet; m, multiplet; br, broad.

LRMS means low resolution mass spectrum.
HRMS means high resolution mass spectrum.
Room temperature means 20°–25° C.

EXAMPLE 1

5-(3-Hydroxy-3-methyl-1-but-1-enyl)-3-(N-methyl-2(R)-pyrrolidinylmethyl)-1H-indole A stirred solution of 5-bromo-3-(N-methyl-2(R)-pyrrolidinylmethyl)-1H-indole (WO-A-92/06973; 879 mg, 3.0 mmol), 2-methylbut-3-en-2-ol (0.408 ml, 3.9 mmol), tri-o-tolylphosphine (273 mg, 0.90 mmol), palladium(II) acetate (45 mg, 0.20 mmol), triethylamine (0.84 ml, 6.0 mmol) and acetonitrile (50 ml), under nitrogen, was heated under reflux for 24 hours, allowed to cool, then partitioned between ethyl acetate and 2M aqueous sodium carbonate solution. The organic phase was separated, washed sequentially with 2M aqueous sodium carbonate solution (×2) and brine (×1), dried (Na$_2$SO$_4$) and evaporated under reduced pressure. The crude product was purified by column chromatography on silica gel, eluting with a solvent gradient of 0.880 aqueous ammonia:methanol: dichloromethane (0:5:95 to 0.5:5:95), to afford the title compound as a solid (226 mg), m.p. 155°–158° C. Rf 0.10 (SS 1). [α]$_D^{25}$+81° (c=0.1, CH$_3$OH). Found: C,75.27; H,8.96; N,8.99. C$_{19}$H$_{26}$N$_2$O; 0.25 H$_2$O requires C,75.33; H,8.82; N,9.25%.

EXAMPLE 2

5-(3-Hydroxy-3-methyl-1-butyl)-3-(N-methyl-2(R)-pyrrolidinylmethyl)-1H-indole

A solution of the title compound of Example 1 (500 mg, 1.65 mmol) in ethanol (50 ml) was hydrogenated over 5% palladium on charcoal (250 mg) at 15 p.s.i. (1.04 bar) and room temperature for 18 hours, then filtered. Evaporation of the filtrate under reduced pressure yielded an oil, which was azeotroped with dichloromethane (2×50 ml) to give a white foam (488 mg). Purification of the foam by column chromatography on silica gel, eluting with a solvent gradient of 0.880 aqueous ammonia:methanol:dichloromethane (0:0:100 to 0:5:95 to 0.5:3.5:96), provided the title compound as a white solid (318 mg), m.p. 125°–126° C. [α]$_D^{25}$+93° (c=0.1, CH$_3$OH). Found: C,74.61; H,9.33; N,8.92. C$_{19}$H$_{28}$N$_2$O; 0.05 CH$_2$Cl$_2$; 0.17 H$_2$O requires C,74.36; H,9.31; N,9.11%.

EXAMPLE 3

5-(3-Hydroxy-1-but-1-enyl)-3-(N-methyl-2(R)-pyrrolidinylmethyl)-1H-indole

Obtained by a procedure similar to that described in Example 1, using but-3-en-2-ol as the appropriate alkene, as a foam. Rf 0.10 (SS 2). Found: C,72.53; H,8.23; N,9.28. C$_{18}$H$_{24}$N$_2$O; 0.20 CH$_2$Cl$_2$ requires C,72.53; H,8.16; N,9.30%.

EXAMPLE 4

5-(3-Hydroxy-1-butl)-3-(N-methyl-2-(R)-pyrrolidinylmethyl)-1H-indole

Obtained from the title compound of Example 3 by a procedure similar to that described in Example 2, but using 10% palladium on charcoal as catalyst, as a foam. Rf 0.80 (SS 4). [α]$_D^{25}$+76° (c=0.1, CH$_3$OH). Found: C,73.95; H,9.03; N,9.70. C$_{18}$H$_{26}$N$_2$O; 0.25 H$_2$O requires C,74.31; H,9.18; N,9.63%.

EXAMPLE 5

5-[2-(1-Hydroxycyclopentyl)ethenyl]-3-(N-methyl-2(R)-pyrrolidinylmethyl)-1H-indole (a) 1-Vinylcyclopentanol A solution of cyclopentanone (7.5 g, 0.09 mol) in dry tetrahydrofuran (30 ml) was added dropwise to a stirred 1M solution of vinylmagnesium bromide in tetrahydrofuran (99 ml, 0.099 mol) under nitrogen at about 0° C. The reaction mixture was stirred at room temperature for 18 hours, cooled to about 0° C., treated drop-wise with saturated aqueous ammonium chloride solution (45 ml) and exhaustively extracted with ethyl acetate. The combined extracts were dried (Na$_2$SO$_4$) and evaporated under reduced pressure, then the residual liquid distilled to give 1-vinylcyclopentanol as a colourless oil (5.68 g), b.p. 92°–100° C./100 mm. Rf 0.40 (SS 3).

(b)

The title compound was obtained by a procedure similar to that described in Example 1, using 1-vinylcyclopentanol as the appropriate alkene, as an oil. Rf 0.30 (SS 2). [α]$_D^{25}$+89° (c=0.1, CH$_3$OH). Found: C,76.15; H,8.50; N,8.62. C$_{21}$H$_{28}$N$_2$O; 0.33 H2O requires C,76.31; H,8.74; N,8.48%.

EXAMPLE 6

5-[2-(1-Hydroxycyclopentyl)ethyl]-3-(N-methyl-2(R)-pyrrolidinylmethyl)-1H-indole Obtained from the title compound of Example 5 by a procedure similar to that described in Example 2 as a foam. Rf 0.30 (SS 2). $[\alpha]_D^{25}+70°$ (c=0.1, $CH_3OH$). Found: C,75.12; H,9.12; N,8.51. $C_{21}H_{30}N_2O$; 0.50 $H_2O$ requires C,75.17; H,9.31; N,8.35%.

EXAMPLE 7

5-[2-(1-Hydroxycyclohexyl)ethenyl]-3-(N-methyl-2(R)-pyrrolidinylmethyl)-1H-indole (a) 1-Vinylcyclohexanol Obtained by a procedure similar to that described in Example 5(a), using cyclohexanone as the appropriate ketone, as an oil. Instead of distillation, the crude product was purified by column chromatography on silica gel, eluting with ether:hexane (2.5:100). Rf 0.50 (SS 3). Found: C,75.83; H,11.91. $C_8H_{14}O$; 0.04 $(C_2H_5)_2O$ requires C,75.53; H,11.89%.

(b)

The title compound was obtained by a procedure similar to that described in Example 1, using 1-vinylcyclohexanol as the appropriate alkene, as an oil.

Rf 0.17 (SS 2). $[\alpha]_D^{25}+52°$ (c=0.1, $CH_3OH$). Found: C,75.91; H,8.85; N,8.06. $C_{22}H_{30}N_2O$; 0.50 $H_2O$ requires C,76.03; H,9.04; N,7.94%.

EXAMPLE 8

5-[2-(1-Hydroxycyclohexyl)ethyl]-3-(N-methyl-2(R)-pyrrolidinylmethyl-1H-indole Obtained from the title compound of Example 7 by a procedure similar to that described in Example 2 as a foam. Rf 0.25 (SS 2). $[\alpha]_D^{25}+56°$ (c=0.1, $CH_3OH$). Found: C,74.24; H,8.86; N,8.04. $C_{22}H32N_2O$; 0.20 $CH_2Cl_2$ requires C,74.57; H,9.13; N,7.84%.

EXAMPLE 9

5-(3-Ethyl-3-hydroxy-1-pent-1-enyl)-3-(N-methyl-2(R)-pyrrolidinylmethyl)-1H-indole (a) 3-Ethylpent-1-en-3-ol Obtained by a procedure similar to that described in Example 5(a), using pentan-3-one as the appropriate ketone, as an oil. Purification was effected by column chromatography on silica gel, eluting with ether:hexane (1:1). Rf 0.40 (SS 3).

(b)

The title compound was obtained by a procedure similar to that described in Example 1, using 3-ethylpent-1-en-3-ol as the appropriate alkene, as an oil. Rf 0.25 (SS 2). $[\alpha]_D^{25}+72°$ (c=0.1, $CH_3OH$). Found: C,74.72; H,8.56; N,8.68. $C_{21}H_{30}N_2O$: 0.67 $H_2O$ requires C,74.51; H,8.93; N,8.28%.

EXAMPLE 10

5-(3-Ethyl-3-hydroxy-1-pentyl)-3-(N-methyl-2(R)-pyrrolidinylmethyl)-1H-indole Obtained from the title compound of Example 9 by a procedure similar to that described in Example 2 as a foam. Rf 0.25 (SS 2). $[\gamma]_D^{25}+64°$ (c=0.1, $CH_3OH$). Found: C,72.31; H,9.15; N,8.31. $C_{21}H_{32}N_2O$; 0.25 $CH_2Cl_2$; 0.20 $H_2O$ requires C,72.22; H,9.38; N,7.93%.

EXAMPLE 11

5-2-(4-Hydroxy-4-tetrahydropyranyl)ethenyl]-3-(N-methyl-2(R)-pyrrolidinylmethyl)-1H-indole (a) 4-Vinyl tetrahydro-4H-pyran-4-ol Obtained by a procedure similar to that described in Example 5(a), using tetrahydro-4H-pyran-4-one as the appropriate ketone, as an oil. Purification was effected by column chromatography on silica gel, eluting with ethyl acetate:hexane (1:3). Rf 0.35 (SS 5). Found: C,63.56; H,9.29. $C_7H_{12}O_2$; 0.25 $H_2O$ requires C,63.37; H,9.50%.

(b)

The title compound was obtained by a procedure similar to that described in Example 1, using 4-vinyl tetrahydro-4H-pyran-4-ol as the appropriate alkene, as a foam. Rf 0.28 (SS 6). $[\alpha]_D^{25}+80°$ (c=0.1, $CH_3OH$). Found: C,70,33; H,8.02; N,8.09. $C_{21}H_{28}N_2O_2$; 0.25 $CH_2Cl_2$ requires C,70.57; H,7.94; N,7.74%.

EXAMPLE 12

5-[2-(4-Hydroxy-4-tetrahydropyranyl)ethyl]-3-(N-methyl-2(R)-pyrrolidinylmethyl)-1H-indole Obtained from the title compound of Example 11 by a procedure similar to that described in Example 2, but using 10% palladium on charcoal as catalyst, as a foam. Rf 0.27 (SS 6). $[\alpha]_D^{25}+51°$ (c=0.1, $CH_3OH$). Found: C,70.58; H,8.71; N,7.71. $C_{21}H_{30}N_2O_2$; 0.20 $CH_2Cl_2$ requires C,70.83; H,8.52; N,7.79%.

EXAMPLE 13

5-[2-(1-Hydroxycyclobutyl)ethenyl]-3-(N-methyl-2(R)-pyrrolidinylmethyl)-1H-indole (a) 1-Vinylcyclobutanol Obtained by a procedure similar to that described in Example 5(a), using cyclobutanone as the appropriate ketone, as an oil. Rf 0.40 (SS 3).

(b)

The title compound was obtained by a procedure similar to that described in Example 1, using 1-vinylcyclobutanol as the appropriate alkene, as an oil. Rf 0.30 (SS 2). $[\alpha]_D^{25}+73°$ (c=0.1, $CH_3OH$). Found: C,77.60; H,8.66; N,8.83. $CH_{20}H_{26}N_2O$ requires C,77.38; H,8.44; N,9.03%

EXAMPLE 14

5-[2-(1-Hydroxycyclobutyl)ethyl]-3-(N-methyl-2(R)-pyrrolidinylmethyl)-1H-indole Obtained from the title compound of Example 13 by a procedure similar to that described in Example 2, but using 10% palladium on charcoal as catalyst, as a foam. Rf 0.40 (SS 7). $[\alpha]_D^{25}+65°$ (c=0.1, $CH_3OH$). LRMS: m/z 313.4 $(M+1)^+$.

EXAMPLE 15

5-(4-Hydroxy-1-pent-1-enyl)-3-(N-methyl-2(R)-pyrrolidinylmethyl)-1H-indole

Obtained by a procedure similar to that described in Example 1, using pent-4-en-2-ol as the appropriate alkene, as a solid. Rf 0.15 (SS 7). Found: C,75.64; H,8.74; N,8.51. $C_{19}H_{26}N_2O$; 0.30 $H_2O$ requires C,75.10; H,8.82; N,9.21%.

EXAMPLE 16

5-(4-Hydroxy-1-pentyl)-3-(N-methyl-2(R)-pyrrolidinylmethyl)-1H-indole

Obtained from the title compound of Example 15 by a procedure similar to that described in Example 2, but using 10% palladium on charcoal as catalyst, as a foam. Rf 0.16 (SS 7). Found: C,75.18; H,8.91; N,9.07. $C_{19}H_{28}N_2O$; 0.17 $H_2O$ requires C,75.19; H,9.41; N,9.22%.

EXAMPLE 17

5-(4-Hydroxy-1-but-1-enyl)-3-(N-methyl-2(R)-pyrrolidinylmethyl)-1H-indole

Obtained by a procedure similar to that described in Example 1, using but-3-en-1-ol as the appropriate alkene, as a foam. Rf 0.13 (SS 7). $[\alpha]_D^{25}+9°$ (c=0.1, $CH_3OH$). Found: C,75.67; H,8.30; N,9.72. $C_{18}H_{24}N_2O$ requires C,76.02; H,8.51; N,9.84%.

EXAMPLE 18

5-(4-Hydroxy-1-butyl)-3-(N-methyl-2(R)-pyrrolidinylmethyl)-1H-indole

Obtained from the title compound of Example 17 by a procedure similar to that described in Example 2, but using 10% palladium on charcoal as catalyst, as a foam. Rf 0.14 (SS 7). Found: C,71.04; H,8.27; N,8.61. $C_{18}H_{26}N_2O$; 0.33 $CH_2Cl_2$ requires C,70.47; H,8.59; N,8.97%.

EXAMPLE 19

5-(4-Hydroxy-4-methyl-1-pent-1-enyl)-3-(N-methyl-2(R)-pyrrolidinylmethyl)-1H-indole The title compound was obtained by a procedure similar to that described in Example 1, using 2-methylpent-4-en-2-ol (J. Chem. Soc. Perkin Trans. II, 1987, 1683) as the appropriate alkene, as a foam. Rf 0.17 (SS 7). Found: C,75.30: H,9.27; N,8.90. $C_{20}H_{28}N_2O$; 0.33 $H_2O$ requires C,75.57; H,9.06; N,8.80%.

EXAMPLE 20

5-(4-Hydroxy-4-methyl-1-pentyl)-3-(N-methyl-2(R)-pyrrolidinylmethyl)-1H-indole

Obtained from the title compound of Example 19 by a procedure similar to that described in Example 2, but using 10% palladium on charcoal as catalyst, as a foam. Rf 0.19 (SS 7). Found: C,73.41; H,9.27; N,8.02. $C_{20}H_{30}N_2O$; 0.20 $CH_2Cl_2$ requires C,73.19; H,9.24; N,8.44%.

EXAMPLE 21

5-[3-(1-Hydroxycyclopentyl)-1-prop-1-enyl]-3-(N-methyl-2(R)-pyrrolidinylmethyl)-1H-indole (a) 1-Allylcyclopentanol Obtained by a procedure similar to that described in the literature reference of Example 19, using cyclopentanone as the appropriate ketone, as an oil and used without further purification in the following step.

(b)

The title compound was obtained by a procedure similar to that described in Example 1, using 1-allylcyclopentanol as the appropriate alkene, as a solid. Rf 0.18 (SS 7). $[\alpha]_D^{25}+87°$ (c=0.1, $CH_3OH$). Found: C,77.81; H,8.95; N,8.37. $C_{22}H_{30}N_2O$ requires C,78.06; H,8.93; N,8.27%.

EXAMPLE 22

5-[3-(1-Hydroxycyclopentyl)-1-propyl]-3-(N-methyl-2(R)-pyrrolidinylmethyl)-1H-indole Obtained from the title compound of Example 21 by a procedure similar to that described in Example 2, but using 10% palladium on charcoal as catalyst, as a solid. Rf 0.19 (SS 9). Found: C,70.90; H,8.56; N,7.23. $C_{22}H_{32}N_2O$; 0.50 $CH_2Cl_2$ requires C,70.56; H,8.68; N,7.31%.

EXAMPLE 23

5-(3-Hydroxy-3-methyl-1-but-1-enyl)-3-(2(R)-pyrrolidinylmethyl)-1H-indole

Obtained from 5-bromo-3-(2(R)-pyrrolidinylmethyl)-1H-indole (Preparation 2) and 2-methylbut-3-en-2-ol, by a procedure similar to that described in Example 1, as a solid. Rf 0.20 (SS 12). $[\alpha]_D^{25}-40°$ (c=0.1, $CH_3OH$).

EXAMPLE 24

3-(N-Cyclopropylmethyl-2(R)-pyrrolidinylmethyl)-5-(3-hydroxy-3-methyl-1-but-1-enyl)-1H-indole The title compound was preparedby either of the following methods.

(A)

(a) 5-Bromo-3-(N-cyclopropylmethyl-2(R)-pyrrolidinylmethyl)-1H-indole

A stirred mixture of 5-bromo-3-(2(R)-pyrrolidinylmethyl)-1H-indole (Preparation 2; 1.84 g, 6.3 mmol), cyclopropylmethyl bromide (0.67 ml, 6.9 mmol), anhydrous sodium carbonate (0.73 g, 6.9 mmol), sodium iodide (1.0 g, 6.7 mmol) and 1,2-dimethoxyethane (10 ml), under nitrogen, was heated under reflux for 14 hours, allowed to cool, then partitioned between ethyl acetate and 2M aqueous sodium carbonate solution. The organic phase was separated, washed with 2M aqueous sodium carbonate solution, dried ($Na_2SO_4$) and evaporated under reduced pressure. The residue was purified by column chromatography on silica gel, eluting with 0.880 aqueous ammonia:methanol: dichloromethane (0.05:10:90), to provide the required product as a foam (2.09 g). Rf 0.24 (SS 6). $[\alpha]_D^{25}+72°$ (c=0.1, $CH_3OH$). Found: C,61.22; H,6.40; N,8.39. $C_{17}H_{21}BrN_2$ requires C,61.26; H,6.35; N,8.41%.

(b)

The title compound was obtained from the previous product (Example 24(A)(a)) by a procedure similar to that described in Example 1, using 2-methylbut-3-en-2-ol as the appropriate alkene, as a foam. Rf 0.48 (SS 7) $[\alpha]_D^{25}+59°$ (c=0.1, CH$_3$OH). Found: C,75.52; H,8.66; N,8.00. C$_{22}$H$_{30}$N$_2$O; 0.17 CH$_2$Cl$_2$ requires C,75.60; H,8.68; N,7.95%.

(B)

The title compound was obtained from the title compound of Example 23 and cyclopropylmethyl bromide, by a procedure similar to that described in Example 24(A)(a), as a solid. Rf 0.44 (SS 7). $[\alpha]_D^{25}+53°$ (c=0.1, CH$_3$OH). Found: C,74.17; H,9.11; N,7.68. C$_{22}$H$_{30}$N$_2$O; 0.125 CH$_2$Cl$_2$; 0.50 H$_2$O requires C,74.21; H,8.79; N,7.82%.

EXAMPLE 25

3-(N-Cyclopropylmethyl-2(R)-pyrrolidinylmethyl)-5-(3-hydroxy-3-methyl-1-butyl)-1H-indole Obtained from the title compound of Example 24 by a procedure similar to that described in Example 2, but using 10% palladium on charcoal as catalyst and 30 p.s.i. (2.07 bar) hydrogen pressure, as a foam. Rf 0.49 (SS 9). Found: C,75.94; H,9.24; N,7.53. C$_{22}$H$_{32}$N$_2$O; 0.15 CH$_2$Cl$_2$ requires C,75.31; H,9.21; N,7.92%.

EXAMPLE 26

5-(3-Hydroxy-3-methyl-1-but-1-enyl)-3-[N-(2-propyl)-2(R)-pyrrolidinylmethyl]-1H-indole (a) 5-Bromo-3-[N-(2-propyl)-2(R)-pyrrolidinylmethyl]-1H-indole Obtained by a procedure similar to that described in Example 24(A)(a), using 2-iodopropane as the appropriate alkylating agent, as a foam. Rf 0.24 (SS 13). $[\alpha]_D^{25}+66°$ (c=0.1, CH$_3$OH). Found: C,59.81; H,6.99; N,8.50. C$_{16}$H$_{21}$BrN$_2$ requires C,59.82; H,6.59; N,8.72%.

(b)

The title compound was obtained from the previous product (Example 26(a)) by a procedure similar to that described in Example 1, using 2-methylbut-3-en-2-ol as the appropriate alkene, as a foam. Rf 0.07 (SS 13). $[\alpha]_D^{25}+56°$ (c=0.1, CH$_3$OH). Found: C,74.67; H,9.49; N,8.09. C$_{21}$H$_{30}$N$_2$O; 0.70 H$_2$O requires C,74.38; H,9.33; N,8.26%.

EXAMPLE 27

5-(3-Hydroxy-3-methl-1-but-1-enyl)-3-[N-(2-methoxyethyl)-2(R)-pyrrolidinylmethyl]-1H-indole (a) 5-Bromo-3-[N-(2-methoxyethyl)-2(R)-pyrrolidinylmethyl]-1H-indole Obtained by a procedure similar to that described in Example 24(A)(a), using 2-methoxyethyl bromide as the appropriate alkylating agent, as an oil. Rf 0.45 (SS 11). Found: C,57.25; H,6.41; N,8.14. C$_{16}$H$_{21}$BrN$_2$O requires C,56.98; H,6.28; N,8.31%.

(b)

The title compound was obtained from the previous product (Example 27(a)) by a procedure similar to that described in Example 1, using 2-methylbut-3-en-2-ol as the appropriate alkene, as a foam. Rf 0.51 (SS 7). $[\alpha]_D^{25}+46°$ (c=0.1, CH$_3$OH). Found: C,67.21; H,8.15; N,7.34. C$_{21}$H$_{30}$N$_2$O$_2$; 0.50 CH$_2$Cl$_2$ requires C,67.08; H,8.12; N,7.27%. LRMS: m/z 343.5 (M+1)$^+$.

EXAMPLE 28

3-[N-(2-Carbamoylethyl)-2(R)-pyrrolidinylmethyl]-5-(3-hydroxy-3-methyl-1-but-1-enyl)-1H-indole (a) 5-Bromo-3-[N-(2-carbamoylethyl)-2(R)-pyrrolidinylmethyl]-1H-indole A stirred mixture of 5-bromo-3-(2(R)-pyrrolidinylmethyl)-1H-indole (Preparation 2; 600 mg, 2.1 mmol), acrylamide (168 mg, 2.4 mmol), triethylamine (0.60 ml) and 1,2-dimethoxyethane (11.9 ml), under nitrogen, was heated under reflux for 8 hours, allowed to cool, then partitioned between ethyl acetate (400 ml) and water (400 ml). The organic phase was separated, washed with water (400 ml), dried (Na$_2$SO$_4$) and evaporated under reduced pressure. The residue was purified by column chromatography on silica gel, eluting with a solvent gradient of 0.880 aqueous ammonia:methanol: dichloromethane (0.1:10:90 to 0.4:10:90), to afford the required product as a foam. Rf 0.26 (SS 7). $[\alpha]_D^{25}+59°$ (c=0.1, CH$_3$OH).

(b)

The title compound was obtained from the previous product (Example 28(a)) by a procedure similar to that described in Example 1, using 2-methylbut-3-en-2-ol as the appropriate alkene, as a white solid. Rf 0.08 (SS 7). $[\alpha]_D^{25}+70°$ (c=0.1, CH$_3$OH)- Found: C,67.37; H,8.32; N,10.71. C$_{21}$H$_{29}$N$_3$O$_2$; 0.22 CH$_2$Cl$_2$; 0.25 H$_2$O requires C,67.32; H,7.97; N,11.10%.

EXAMPLE 29

5-(3-Hydroxy-3-methyl-1-butyl)-3-(2(R)-pyrrolidinylmethyl)-1H-indole (a) 3-(N-Benzyloxycarbonyl-2(R)-pyrrolidinylmethyl)-5-(3-hydroxy-3-methyl-1-but-1-enyl)-1H-indole Obtained from 3-(N-benzyloxycarbonyl-2(R)-pyrrolidinylmethyl)-5-bromo-1H-indole (Preparation 1) and 2-methylbut-3-en-2-ol, by a procedure similar to that described in Example 1, as a foam. Rf 0.40 (SS 5). $[\alpha]_D^{25}-10°$ (c=0.1, CH$_3$OH). Found: C,73.72; H6.92; N,6.18. C$_{26}$H$_{30}$N$_2$O$_3$; 0.10 CH$_2$Cl$_2$ requires C,73.41; H,7.13; N,6.56%.

(b)

The title compound was obtained from the previous product (Example 29(a)) by a procedure similar to that described in Example 2, but using 10% palladium on charcoal as catalyst, as a foam. Rf 0.10 (SS 7). $[\alpha]_D^{25}-8°$ (c=0.1, CH$_3$OH). Found: C,70.77; H,8.96; N,9.09. C$_{18}$H$_{26}$N$_2$O; H$_2$O requires C,71.02; H,9.27; N,9.20%.

EXAMPLE 30

5-(3-Hydroxy-3-methyl-1-butyl)-3-{N-[2-(4-pyridyl)ethyl]-2(R)-pyrrolidinylmethyl}-1H-indole Obtained from the title compound of Example 29 and 4-vinylpyridine by a procedure similar to that described in Example 28(a), except that no triethylamine was used in the reaction, as a foam. Rf 0.18 (SS 13). $[\alpha]_D^{25}+25°$ (c=0.1, CH$_3$OH). Found: C,74.94; H,8.71; N,10.20. C$_{25}$H$_{33}$N$_3$O; 0.50 H$_2$O requires C,74.96; H,8.56; N,10.49%. LRMS: m/z 392.5 (M+1)$^+$.

EXAMPLE 31

3-{N-[2-(Ethylsulphonyl)ethyl]-2(R)-pyrrolidinylmethyl}-5-(3-hydroxy-3-methyl-1-butyl)-1H-indole Obtained from the title compound of Example 29 and ethyl vinyl sulphone, by a procedure similar to that described in Example 28(a), as a foam. Rf 0.42 (SS 13). $[\alpha]_D^{25} +40°$ (c=0.1, CH$_3$OH). Found: C,64.20; H,8.54; N,6.88; S,7.94. C$_{22}$H$_{34}$N$_2$O$_3$S; 0.25 H$_2$O requires C,64.28; H,8.46; N,6.81; S,7.80%.

EXAMPLE 32

5-(3-Hydroxy-3-methyl-1-pentyl)-3-(2(R)-pyrrolidinylmethyl)-1H-indole (a) 3-(N-Benzyloxycarbonyl-2(R)-pyrrolidinylmethyl)-5-(3-hydroxy-3-methyl-1-pent-1-enyl)-1H-indole Obtained from 3-(N-benzyloxycarbonyl-2(R)-pyrrolidinylmethyl)-5-bromo-1H-indole (Preparation 1) and 3-methyl-1-penten-3-ol, by a procedure similar to that described in Example 1, as a foam. Rf 0.90 (SS 7). $[\alpha]_D^{25} -9°$ (c=0.1, CH$_3$OH). Found: C,71.27; H,6.98; N,5.83. C$_{27}$H$_{32}$N$_2$O$_3$; 0.33 CH$_2$Cl$_2$ requires C,71.23; H,7.14; N,6.08%.

(b)

The title compound was obtained from the previous product (Example 32(a)) by a procedure similar to that described in Example 2, but using 10% palladium on charcoal as catalyst, as a foam. Rf 0.10 (SS 7). $[\alpha]_D^{25} -12°$ (c=0.1, CH$_3$OH). Found: C,73.41; H,9.63; N,8.86. C$_{19}$H$_{28}$N$_2$O; 0.50 H$_2$O requires C,73.74; H,9.44; N,9.05%. LRMS: m/z 301.2 (M+1)$^+$.

EXAMPLE 33

5-[2-(1-Hydroxycyclopentyl)ethyl]-3-(2(R)-pyrrolidinylmethyl)-1H-indole (a) 3-(N-Benzyloxycarbonyl-2(R)-pyrrolidinylmethyl)-5-[2-(1-hydroxycyclopentyl)ethenyl]-1H-indole Obtained by a procedure similar to that described in Example 1, from 3-(N-benzyloxycarbonyl-2(R)-pyrrolidinylmethyl)-5-bromo-1H-indole (Preparation 1) and 1-vinylcyclopentanol (Example 5(a)), as a foam. Rf 0.40 (SS 10). $[\alpha]_D^{25} -31°$ (c=0.1, CH$_3$OH). Found: C,75.58; H,7.24; N,6.22. C$_{28}$H$_{32}$N$_2$O$_3$ requires C,75.64; H,7.26; N,6.30%.

(b)

The title compound was prepared from the previous product (Example 33(a)) by either of the following methods.

(A)

Obtained by a procedure similar to that described in Example 2, but using 10% palladium on charcoal as catalyst, as a foam. Rf 0.15 (SS 7). $[\alpha]_D^{25} -13°$ (c=0.1, CH$_3$OH). Found: C,73.32; H,8.89; N,8.51. C$_{20}$H$_{28}$N$_2$O; 0.20 CH$_2$Cl$_2$ requires C,73.64; H,8.69; N,8.50%.

(B)

A solution of the title compound of Example 29(a) (290 mg, 0.65 mmol) in ethanol (2.5 ml) was added dropwise to a stirred mixture of palladium(II) acetate (30 mg, 0.13 mmol), triethylsilane (0.6 ml, 3.8 mmol) and triethylamine (0.5 ml, 3.6 mmol) under nitrogen at room temperature. After 72 hours, the reaction mixture was filtered, the filtrate evaporated under reduced pressure and the residue azeotroped with dichloromethane. Purification of the crude product by column chromatography on silica gel, eluting with a solvent gradient of 0.880 aqueous ammonia:methanol:dichloromethane (0:0:100 to 0:10:90 to 1:10:90), afforded the title compound as a foam (125 mg). Rf 0.10 (SS 7). $[\alpha]_D^{25} -18°$ (c=0.1, CH$_3$OH). Found: C,74.01; H,9.01; N,8.58. C$_{20}$H$_{28}$N$_2$O; 0.06 CH$_2$Cl$_2$; 0.33 H$_2$O, requires C,74.36; H,8.96; N,8.64%.

EXAMPLE 34

5-[2-(1-Hydroxycyclopentyl)ethenyl]-3-{N-[2-(N,N-dimethylcarbamoyl)ethyl]-2(R)-pyrrolidinylmethyl}-1H-indole (a) 5-Bromo-3-{N-[2-(N,N-dimethylcarbamoyl)ethyl]-2-(R)-pyrrolidinylmethyl}-1H-indole Obtained from 5-bromo-3-(2(R)-pyrrolidinylmethyl)1H-indole (Preparation 2) and N,N-dimethylacrylamide, by a procedure similar to that described in Example 28(a), as a foam. Rf 0.58 (SS 7). Found: C,55.53; H,6.18; N,10.66. C$_{18}$H$_{24}$BrN$_3$O; 0.20 CH$_2$Cl$_2$ requires C,55.30; H,6.22; N,10.63%.

(b)

The title compound was obtained from the previous product (Example 34(a)) and 1-vinylcyclopentanol (Example 5(a)), by a procedure similar to that described in Example 1, as a foam. Rf 0.40 (SS 7). $[\alpha]_D^{25} +27°$ (c=0.1, CH$_3$OH). Found: C,70.55; H,8.74; N,9.47. C$_{25}$H$_{35}$N$_3$O$_2$; 0.125 CH$_2$Cl$_2$; 0.50 H$_2$O requires C,70.31; H,8.51; N,9.79%. LRMS: m/z 410.7 (M+1)$^+$.

Trituration of a sample with ethyl acetate, followed by crystallisation from ethyl acetate, provided a solid, m.p. 151°–152° C. Found: C,73.23; H,8.48; N,9.93. C$_{25}$H$_{35}$N$_3$O$_2$ requires C,73.31; H,8.61; N,10.23%.

EXAMPLE 35

5-[2-(1-Hydroxycyclopentyl)ethyl]-3-{N-[2-(N,N-dimethylcarbamoyl)ethyl]-2(R)-pyrrolidinylmethyl}-1H-indole The title compound was obtained by either of the following methods.

(A)

Obtained from the title compound of Example 33 and N,N-dimethylacrylamide, using a procedure similar to that described in Example 28(a), as a foam. Rf 0.37 (SS 7). $[\alpha]_D^{25} +29°$ (c=0.1, CH$_3$OH). Found: C,70.08; H,9.06; N,9.59. C$_{25}$H$_{37}$N$_3$O$_2$; 0.25 CH$_2$Cl$_2$ requires C,70.06; H,8.73; N,9.71%.

(B)

Obtained from the title compound of Example 34 by a procedure similar to that described in Example 2, but using 10% palladium on charcoal as catalyst, as a foam. $[\alpha]_D^{25} +31°$ (c=0.1, CH$_3$OH). Rf 0.35 (SS 7). Found: C,69.62; H,8.75; N,9.31. C$_{25}$H$_{37}$N$_3$O$_2$; 0.25 CH$_2$Cl$_2$; 0.17 H$_2$O requires C,69.58; H,8.75; N,9.64%.

Crystallisation of a sample from ethyl acetate-water provided a solid, m.p. 84°–85° C. Found: C,69.78; H,9.32; N,9.79. C$_{25}$H$_{37}$N$_3$O$_2$; H$_2$O requires C,69.89; H,9.15; N,9.78%. LRMS: m/z 412.0 (M+1)$^+$.

The hydrochloride salt was obtained as a solid, m.p. 182°–183° C. (acetone). Rf 0.24 (SS 7). $[\alpha]_D^{25} -52°$ (c=0.1, CH$_3$OH). Found: C,66.00; H,8.65; N,8.98. C$_{25}$H$_{37}$N$_3$O$_2$; HCl requires C,65.70; H,8.49; N,9.19%.

EXAMPLE 36

5-[2-(1-Hydroxycyclobutyl)ethyl]-3-(2(R)-pyrrolidinylmethyl)-1H-indole (a) 3-(N-Benzyloxycarbonyl-2(R)-pyrrolidinylmethyl)-5-[2-(1-hydroxycyclobutyl)ethenyl]-1H-indole Obtained from 3-(N-benzyloxycarbonyl-2(R)-pyrrolidinylmethyl)-5-bromo-1H-indole (Preparatidn 1) and 1-vinylcyclobutanol (Example 13(a)), by a procedure similar to that described in Example 1, as an oil. Rf 0.50 (SS 7). Found: C,68.35; H,6.73; N,5.29. $C_{27}H_{30}N_2O_3$; 0.67 $CH_2Cl_2$ requires C,68.18; H,6.48; N,5.75%.

(b)

The title compound was prepared from the previous product (Example 36(a)) by a procedure similar to that described in Example 2, but using 10% palladium on charcoal as catalyst, as a foam. Rf 0.11 (SS 4). $[\alpha]_D^{25}-22°$ (c=0.1, $CH_3OH$). Found: C,74.33; H,8.84; N,8.82. $C_{19}H_{26}N_2O$; 0.12 $CH_2Cl_2$ requires C,74.41; H,8.57; N,9.08%. LRMS: m/z 299.3 $(M+1)^+$.

EXAMPLE 37

5-(3-Oxo-1-butyl)-3-(2(R)-pyrrolidinylmethyl)-1H-indole (a) 3-(N-Benzyloxycarbonyl-2(R)-pyrrolidinylmethyl)-5-(3-oxo-1-but-1-enyl)-1H-indole Obtained by a procedure similar to that described in Example 1, from 3-(N-benzyloxycarbonyl-2(R)-pyrrolidinylmethyl)-5-bromo-1H-indole (Preparation 1) and methyl vinyl ketone, as a foam. Rf 0.60 (SS 7). $[\alpha]_D^{25}-51°$ (c=0.1, $CH_3OH$). Found: C,74.16; H,6.39; N,6.92. $C_{25}H_{26}N_2O_3$ requires C,74.60; H,6.51; N,6.96%.

(b)

The title compound was prepared from the previous product (Example 37(a)) by a procedure similar to that described in Example 2, but using 10% palladium on charcoal as catalyst, as a gum. Rf 0.15 (SS 7). $[\alpha]_D^{25}-8°$ (c=0.1, $CH_3OH$). Found: C,69.63; H,7.75; N,9.30. $C_{17}H_{22}N_2O$; 0.17 $CH_2Cl_2$; 0.67 $H_2O$ requires C,69.52; H,8.04; N,9.45%.

EXAMPLE 38

5-(3-Hydroxy-1-butyl)-3-(2(R)-pvrrolidinylmethyl)-1H-indole

Sodium borohydride (423 mg, 11 mol) was added portionwise over 20 minutes at room temperature, under nitrogen, to a stirred solution of the title compound of Example 37 (1.34 g, 5 mmol) in ethanol (50 ml), then stirring continued for 18 hours. The pH of the resulting reaction mixture was adjusted to 2 with 2N hydrochloric acid, then to 8 with solid sodium carbonate, and the volume reduced to about half by evaporation under reduced pressure, before partitioning between ethyl acetate and water was effected. The organic phase was separated, washed with water, dried ($Na_2SO_4$) and evaporated under reduced pressure to give a foam which was purified by column chromatography on silica gel, eluting with a solvent gradient of 0.880 aqueous ammonia:methanol:dichloromethane (0:0:100 to 0:10:90 to 1:10:90 to 1.5:15:85), to afford the title compound as a foam. Rf 0.10 (SS 7). $[\alpha]_D^{25}-22°$ (c=0.1, $CH_3OH$). Found: C,72.07; H,8.96; N,9.56. $C_{17}H_{24}N_2O$; 0.10 $CH_2Cl_2$; 0.17 $H_2O$ requires C,72.34; H,8.71; N,9.87%.

EXAMPLE 39

5-(3-Hydroxy-1-butyl)-3-[N-(2-methoxyethyl)-2(R)-pyrrolidinylmethyl]-1H-indole The title compound was obtained from the title compound of Example 38 by a procedure similar to that described in Example 24(A)(a), using 2-methoxyethyl bromide as the appropriate alkylating agent, as a gum. Rf 0.30 (SS 7). $[\alpha]_D^{25}+41°$ (c=0.1, $CH_3OH$). Found: C,70.35; H,9.40; N,8.28. $C_{20}H_{30}N_2O_2$; 0.08 $CH_2Cl_2$; 0.25 $H_2O$ requires C,70.52; H,9.04; N,8.19%.

EXAMPLE 40

3-(N-Cyclopropylmethyl-2(R)-pyrrolidinylmethyl)-5-(3-hydroxy-1-butyl)-1H-indole The title compound was obtained from the title compound of Example 38 by a procedure similar to that described in Example 24(A)(a), using cyclopropylmethyl bromide as the appropriate alkylating agent, as a foam. Rf 0.40 (SS 7). $[\alpha]_D^{25}+73°$ (c=0.1, $CH_3OH$). Found: C,75.26; H,9.33; N,8.22. $C_{21}H_{30}N_2O$; 0.50 $H_2O$ requires C,75.18; H,9.31; N,8.35%.

EXAMPLE 41

5-(3-Ethyl-3-hydroxy-1-pentyl)-3-(2(R)-pyrrolidinylmethyl)-1H-indole (a) 3-(N-Benzyloxycarbonyl-2(R)-pyrrolidinylmethyl)-5-(3-ethyl-3-hydroxy-1-pent-1-enyl)-1H-indole Obtained by a procedure similar to that described in Example 1, from 3-(N-benzyloxycarbonyl-2(R)-pyrrolidinylmethyl)-5-bromo-1H-indole (Preparation 1) and 3-ethylpent-1-en-3-ol (Example 9(a)), as a foam. Rf 0.66 (SS 7). $[\alpha]_D^{25}-27°$ (c=0.1, $CH_3OH$). Found: C,75.33; H,+.29; N,5.65. $C_{28}H_{34}N_2O_3$ requires C,75.30; H,7.67; N,6.26%.

(b)

The title compound was prepared from the previous product (Example 41(a)) by a procedure similar to that described in Example 2, but using 10% palladium on charcoal as catalyst, as a foam. Rf 0.12 (SS 7). $[\alpha]_D^{25}-6°$ (c=0.1, $CH_3OH$). Found: C,74.51; H,9.74; N,8.51. $C_{20}H_{30}N_2O$; 0.50 $H_2O$ requires C,74.26; H,9.66; N,8.66%.

EXAMPLE 42

5-(3-Hydroxy-1-but-1-enyl)-3-(N-methyl-4-piperidyl)-1H-indole

Obtained by a procedure similar to that described in Example 1, using 5-bromo-3-(N-methyl-4-piperidyl)-1H-indole (EP-A-0303507) and but-3-en-2-ol, as a foam. Rf 0.50 (SS 4). Found: C,72.85; H,8.22; N,9.17. $C_{18}H_{24}N_2O$; 0.17 $CH_2Cl_2$ requires C,73.08; H,8.22; N,9.38%.

EXAMPLE 43

5-(3-Hydroxy-1-butyl)-3-(N-methyl-4-piperidyl)-1H-indole

Obtained from the title compound of Example 42 by a procedure similar to that described in Example 2, but using 10% palladium on charcoal as catalyst, as a foam. Rf 0.50 (SS 4). C,73.39; H,8.77; N,9.06. $C_{18}H_{26}N_2O$; 0.125 $CH_2Cl_2$ requires C,73.28; H,8.91; N,9.43%.

EXAMPLE 44

5-[2-(1-Hydroxycyclopentyl)ethenyl]-3-(N-methyl-4-piperidyl)-1H-indole

Obtained by analogy with Example 42, using 1-vinylcyclopentanol (Example 5(a)) as the appropriate alkene, as a foam. Rf 0.40 (SS 7). $[\alpha]_D^{25} -21°$ (c=0.1, C$_3$OH). Found: C,70.70; H,8.19; N,7.31. C$_{21}$H$_{28}$N$_2$O; 0.50 CH$_2$Cl$_2$ requires C,70.37; H,7.97; N,7.64%. LRMS: m/z 325 (M+1)$^+$.

EXAMPLE 45

5-[2-(1-Hydroxycyclopentyl)ethyl]-3-(N-methyl-4-piperidyl)-1H-indole

Obtained from the title compound of Example 44, by analogy with Example 43. Rf 0.40 (SS 7). Found: C,73.55; H,8.90; N,8.12. C$_{21}$H$_{30}$N$_2$O; 0.25 CH$_2$Cl$_2$ requires C,73.44; H,8.85; N,8.06%.

EXAMPLE 46

5-(3-Hydroxy-3-methyl-1-but-1-enyl-3-(N-methyl-4-piperidyl)-1H-indole

Obtained by analogy with Example 42, using 2-methylbut-3-en-2-ol as the appropriate alkene, as a white solid, m.p 161°–161.5° C. Rf 0.39 (SS 7). Found: C,66.41; H,7.84; N,7.78. C$_{19}$H$_{26}$N$_2$O; 0.67 CH$_2$Cl$_2$ requires C,66.49; H,7.75; N,7.88%. LRMS: m/z 299.2 (M+1)$^+$.

EXAMPLE 47

3-(2-Aminoethyl)-5-(3-hydroxy-3-methyl-1-but-1-enyl)-1H-indole (a) 5-(3-Hydroxy-3-methyl-1-but-1-enyl)-3-(2-phthalimidoethyl)-1H-indole Obtained by a procedure similar to that described in Example 1, using 5-bromo-3-(2-phthalimidoethyl)-1H-indole (which was prepared as described in U.S. Pat. No. 4,252,803) and 2-methylbut-3-en-2-ol, as a foam. Rf 0.10 (SS 8). Found: C,72.31; H,6.09; N,.7.16. C$_{23}$H$_{22}$N$_2$O$_3$; 0.15 CH$_2$Cl$_2$ requires C,71.82; H,5.81; N,7.23%.

(b)

A solution of hydrazine hydrate (0.5 ml) in ethanol (20 ml) was added, under nitrogen, to a stirred solution of the previous product (Example 47(a); 0.864 g, 2.3 mmol) in ethanol (5 ml) at room temperature, then the resulting solution heated under reflux for 24 hours, allowed to cool and evaporated under reduced pressure. The residue was dissolved in ethyl acetate and this solution washed sequentially with 10% aqueous sodium carbonate solution (×4) and brine, dried (Na$_2$SO$_4$) and evaporated under reduced pressure to provide an oil which, on azeotroping with dichloromethane, followed by purification of the resulting foam by column chromatography using 0.880 aqueous ammonia:ethanol:dichloromethane (1:8:25) as eluant, furnished the title compound as a white foam (250 mg). Rf 0.30 (SS 4). Found: C,71.52; H,8.15; N,11.06. C$_{15}$H$_{20}$N$_2$O; 0.10 CH$_2$Cl$_2$; requires C,71.73; H,8.05; N,11.08%.

EXAMPLE 48

3-(2-Aminoethyl)-5-(3-hydroxy-3-methyl-1-butyl)-1H-indole

Obtained from the title compound of Example 47, by a procedure similar to that described in Example 2, as a white foam. Rf 0.30 (SS 4). Found: C,70.77; H,8.78; N,10.71. C$_{15}$H$_{22}$N$_2$O; 0.05 CH$_2$Cl$_2$; 0.25 H$_2$O requires C,70.86; H,8.92; N,10.98%.

EXAMPLE 49

3-(N-Methyl-2(R)-pyrrolidinylmethyl)-5-(3-oxo-1-but-1-enyl)-1H-indole

Obtained by a procedure similar to that described in Example 1, using methyl vinyl ketone as the appropriate alkene, as a foam. Rf 0.38 (SS 7). $[\alpha]_D^{25} +99°$ (C=0.1, CH$_3$OH). Found: C,71.97; H,7.71; N,9.34. C$_{18}$H$_{22}$N$_2$O; 0.10 CH$_2$Cl$_2$; 0.50 H$_2$O requires C,72.15; H,7.86; N,9.35%.

EXAMPLE 50

3-(N-Methyl-2(R)-pyrrolidinylmethyl)-5-(3-oxo-1-butyl)-1H-indole

Obtained from the title compound of Example 49 by a procedure similar to that described in Example 2, but using 10% palladium on charcoal as catalyst, as a foam. $[\alpha]_D^{25} +83°$ (c=0.1, CH$_3$OH). Found: C,71.61; H,8.36; N,9.02. C$_{18}$H$_{24}$N$_2$O; 0.20 CH$_2$Cl$_2$ requires C,71.84; H,8.16; N,9.30%. LRMS: m/z 285.3 (M+1)$^+$.

EXAMPLE 51

3-(N-Methyl-2(R)-pyrrolidinylmethyl)-5-(3-oxo-1-pent-1-enyl)-1H-indole

Obtained by a procedure similar to that described in Example 1, using ethyl vinyl ketone as the appropriate alkene, as a foam. Rf 0.70 (SS 7). $[\alpha]_D^{25} +115°$ (c=0.1, CH$_3$OH). Found: C,74.85; H,8.22; N,9.47. C$_{19}$H$_{24}$N$_O$; 0.10 CH$_2$Cl$_2$ requires C,75.24; H,7.99; N,9.19%.

EXAMPLE 52

3-(N-Methyl-2(R)-pyrrolidinylmethyl)-5-(3-oxo-1-pentyl)-1H-indole

Obtained from the title compound of Example 51 by a procedure similar to that described in Example 2, but using 10% palladium on charcoal as catalyst, as a gum. Rf 0.70 (SS 7). $[\alpha]_D^{25} +105°$ (c=0.1, C$_3$OH). Found: C,73.04; H,8.66; N,8.97. C$_{19}$H$_{26}$N$_2$O; 0.75 H$_2$O requires C,73.15; H,8.88; N,8.98%.

EXAMPLE 53

5-Acetyl-3-(N-methyl-2(R)-pyrrolidinylmethyl)-1H-indole

The first step was conducted under Heck reaction conditions similar to those described in Example 1, using ethyl vinyl ether as the appropriate alkene.

The crude intermediate, 5-(1-ethoxyethenyl)-3-(N-methyl-2(R)-pyrroldinylmethyl)-1H-indole, was dissolved in 2M hydrochloric acid and the resulting solution stirred for 0.5 hour at room temperature, then basified to pH 9 with 10% aqueous sodium carbonate solution. Extraction with ethyl acetate (×3), followed by drying ($Na_2SO_4$) and evaporation under reduced pressure of the combined extracts, gave the crude product which was purified by column chromatography on silica gel, eluting with 0.880 aqueous ammonia:methanol:dichloromethane (1:12.5:86.5), to afford the title compound. Rf 0.30 (SS 15). Found: C,74.08; H,8.11; N,10.81. $C_{16}H_{20}N_2O$; 0.17 $CH_2Cl_2$ requires C,73.73; H,7.75; N,10.71%.

EXAMPLE 54

3-(N-Methyl-4-piperidyl)-5-(3-oxo-1-pent-1-enyl)-1H-indole hydrobromide

Obtained by analogy with Example 42, using ethyl vinyl ketone as the appropriate alkene, but avoiding treatment with aqueous base during reaction work-up. Instead, the resulting reaction mixture was evaporated under reduced pressure to provide the crude product which was then purified, as usual, by column chromatography on silica gel to furnish the title compound. Rf 0.70 (SS 4). Found: C,58.15; H,6.60; N,7.18. $C_{19}H_{24}N_2O$; HBr; 0.25 $CH_2Cl_2$ requires C,58.01; H,6.45; N,7.03%.

EXAMPLE 55

3-(N-Methyl-4-piperidyl)-5-(3-oxo-1-pentyl)-1H-indole

Obtained from the title compound of Example 54 by a procedure similar to that described in Example 2, but using 10% palladium on charcoal as catalyst. The use of diethylamine:ethyl acetate:hexane (5:25:70) as eluant in the column chromatography on silica gel purification procedure afforded the title compound as the free base. Rf 0.08 (SS 14). Found: C,76.05; H,8.61; N,8.81. $C_{19}H_{26}N_2O$; 0.05 $CH_2Cl_2$; 0.06 $(C_2H_5)_2NH$ requires C,76.47; H,8.78; N,9.39%.

EXAMPLE 56

5-(1-Hydroxyethyl)-3-(N-methyl-4-piperidyl)-1H-indole

A 1.7M solution of t-butyllithium in hexane (8.03 ml, 13.65 mmol) was added dropwise, under nitrogen, to a stirred solution of 5-bromo-3-(N-methyl-4-piperidyl)-1H-indole (EP-A-0303507, 1.0 g, 3.4 mmol) in dry tetrahydrofuran (35 ml) at about −70° C., ensuring that the temperature of the reaction mixture did not rise above −50° C. during the addition. The resulting mixture was allowed to warm to room temperature over a period of 1 hour, then cooled to about −70° C. and treated, dropwise, with a solution of acetaldehyde (0.15 g, 3.4 mmol) in dry tetrahydrofuran (5 ml). After being stirred for a further 0.5 hour at about −70° C., the reaction mixture was quenched with water and allowed to warm to room temperature. The bulk of the organic solvents was removed by evaporation under reduced pressure and the remaining mixture partitioned between ethyl acetate and 10% aqueous ammonium chloride solution. The organic phase was separated, combined with two further ethyl acetate extracts of the aqueous phase, dried ($Na_2SO_4$) and evaporated under reduced pressure to give an oil which was purified by column chromatography on silica gel, eluting with 0.880 aqueous ammonia:methanol:dichloromethane (1:20:79), to provide the title compound which was employed in the following Example without further characterisation.

EXAMPLE 57

5-Acetyl-3-(N-methyl-4-piperidyl)-1H-indole

A mixture of the title compound of Example 56 (160 mg, 0.62 mmol), activated manganese dioxide (1.6 g), dichloromethane (12 ml) and acetonitrile (3 ml) was stirred for 16 hours at room temperature, when a further portion of activated manganese dioxide (0.6 g) was added. After a further 4 days, the reaction mixture was filtered and the filtrate evaporated under reduced pressure. The residue was purified by column chromatography on silica gel, eluting with 0.880 aqueous ammonia:methanol:dichloromethane (1:12.5:86.5), to afford the title compound (35 mg). Rf 0.35 (SS 15). Found: C,73.30; H,7.76; N,10.65. $C_{16}H_{20}N_2O$; 0.17 $CH_2Cl_2$ requires C,73.73; H,7.75; N,10.71%.

EXAMPLE 58

5-(3-Hydroxy-3-methyl-1-butyl)-3-[N-(2-methoxyethyl)-2(R)-pyrrolidinylmethyl]-1H-indole Obtained from the title compound of Example 27 by a procedure similar to that described in Example 2, but using 10% palladium on charcoal as catalyst, as a gum. Rf 0.50 (SS 7). $[\alpha]_D^{25}+64°$ (c=0.1, $CH_3OH$). LRMS: m/z 345.7 $(M+1)^+$.

EXAMPLE 59

5-(3-Hydroxy-3-methyl-1-butyl)-3-[N-(2-propyl)-2(R)-pyrrolidinylmethyl]-1H-indole The title compound was obtained by either of the following methods.

(A)

Obtained from the title compound of Example 26 by a procedure similar to that described in Example2, but using 10% palladium on charcoal as catalyst, as a foam. Rf 0.17 (SS 7). $[\alpha]_D^{25}+24°$ (c=0.1, $CH_3OH$). LRMS: m/z 329.8 $(M+1)^+$.

(B)

Obtained from the title compound of Example 29 and 2-iodopropane by a procedure similar to that described in Example 24(A)(a), but in the presence of 4-dimethylaminopyridine (0.05 equiv), as a foam. Rf 0.24 (SS 13). $[\alpha]_D^{25}+16°$ (c=0.1, $CH_3OH$). Found: C,70.62; H,9.27; N,7.92. $C_{21}H_{32}N_2O$; 0.42 $CH_2Cl_2$ requires C,70.69; H,9.09; N,7.70%.

EXAMPLE 60

5-[2-Hydroxycyclopentyl)ethyl]-3-[N-(2-hydroxyethyl)-2(R)-pyrrolidinylmethyl]-1H-indole A stirred mixture of the title compound of Example 33 (400 mg, 1.3 mmol), ethylene carbonate (124 mg, 1.4 mmol) and dimethylformamide (6 ml) was heated at 100°–120° C. under nitrogen for 48 hours, allowed to cool, then partitioned between ethyl acetate and water. The organic phase was separated, washed with water, dried ($Na_2SO_4$) and evaporated under reduced pressure to furnish an oil (480 mg) which was purified by column chromatography on silica gel, eluting with a solvent gradient of 0.880 aqueous ammonia:methanol:dichloromethane (0:0:100 to 0:10:90 to 1:10:90), to give the title compound as a foam. Rf 0.50 (SS 7). $[\alpha]_D^{25}+55°$ (c=0.1, $CH_3OH$). Found: C,72.60; H,9.34; N,7.58. $C_{22}H_{32}N_2O_2$; 0.50 $H_2O$ requires C,72.29; H,9.10; N,7.67%. LRMS: m/z 357.4 $(M+1)^+$.

EXAMPLE 61

5-(3-Hydroxy-3-methyl-1-butyl)-3-[N-(2-hydroxy-2-methylpropyl)-2(R)-pyrrolidinylmethyl]-1H-indole A stirred solution of the title compound of Example 29 (400 mg, 1.4 mmol), 2,2-dimethyloxirane (0.19 ml, 2.1 mmol) and triethylamine (0.51 ml) in 1,2-dimethoxyethane (10 ml) was heated under reflux under nitrogen for 24 hours. Further quantities of 2,2-dimethyloxirane (0.19 ml, 2.1 mmol) and triethylamine (0.25 ml) were added, heating under reflux continued for a further 68 hours, the same quantities of reagents again added to the reaction mixture, and heating under reflux continued for a further 42 hours, before evaporation under reduced pressure was effected. The residue was partitioned between ethyl acetate and 2M aqueous sodium carbonate solution, then the aqueous phase extracted with ethyl acetate. The combined ethyl acetate solutions were dried ($Na_2SO_4$) and evaporated under reduced pressure, then the residue purified by column chromatography on silica gel, eluting with 0.880 aqueous ammonia:methanol:dichloromethane (0.1:5:95), to afford the title compound as a foam. $[\alpha]_D^{25}$+58° (c=0.1, $CH_3OH$). Found: C,72.88; H,9.62; N,7.54. $C_{22}H_{34}N_2O_2$; 0.25 $H_2O$ requires C,72.79; H,9.58; N,7.72%. LRMS: m/z 359.5 $(M+1)^+$.

EXAMPLE 62

5-[2-(1-Hydroxycyclopentyl)ethyl]-3-[N-(N-methylcarbamoylmethyl)-2(R)-pyrrolidinylmethyl]-1H-indole (a) N-Methyl-2-bromoacetamide A solution of α-bromoacetyl bromide (12.5 ml, 140 mmol) in dichloromethane (17.5 ml) was added dropwise over 1.5 hours to a stirred mixture of 25/30% w/v aqueous methylamine solution (12.5 ml), 6.25M aqueous sodium hydroxide solution (25 ml) and dichloromethane (105 ml) at −10° C. After a further 0.5 hour, the cooling bath was removed and the reaction mixture stirred at room temperature for 2 hours. The organic phase was separated, combined with a dichloromethane extract of the aqueous phase, washed with saturated brine, dried ($NaSO_4$) and evaporated under reduced pressure. The residue was purified by column chromatography on silica gel, eluting with a solvent gradient of ethyl acetate:hexane (0:100 to 70:30), to give the required amide (12.5 g) as a foam. Rf 0.45 (SS 17). $\delta(CDCl_3)$: 2.90(3H,d), 3.92(2H,s), 6.30–6.70.(1H,br s).

(b)

The title compound was prepared from the previous product (Example 62(a)) and the title compound of Example 33, by a procedure similar to that described in Example 24(A)(a), as a foam. Rf 0.50 (SS 7). $[\alpha]_D^{25}$+5° (c=0.1, $CH_3OH$). Found: C,71.68; H,8.77; N,10.73. $C_{23}H_{33}N_3O_2$ requires C,72.02; H,8.67; N,10.96%. LRMS: m/z 384.3 $(M+1)^+$.

EXAMPLE 63

3-[N-(2-Carbamoylethyl)-2(R)-pyrrolidinylmethyl]-5-(3-hydroxy-3-methyl-1-butyl)-1H-indole Obtained from the title compound of Example 28 by a procedure similar to that.described in Example 2, but using 10% palladium on charcoal as catalyst, as a foam. Rf 0.25 (SS 7). $[\alpha]_D^{25}$+61° (c=0.1, $CH_3OH$). Found: C,67.28; H,8.75; N,10.94. $C_{21}H_{31}N_3O_2$; $H_2O$ requires C,67.17; H,8.86; N,11.19%. LRMS: m/z 358.2 $(M+1)^+$.

EXAMPLE 64

5-[2-(1-Hydroxycyclopentyl)ethyl]-3-{N-[2-(N-methylcarbamoyl)ethyl]-2(R)-pyrrolidinylmethyl}-1H-indole (a) N-Methylacrylamide N,N-Diisopropylethylamine (57.8 ml, 331 mmol) was added to a stirred, ice-cooled solution of acryloyl chloride (15 g, 165.7 mmol) in anhydrous dichloromethane (200 ml) followed, portionwise, by methylamine hydrochloride (11.19 g, 165.7 mmol) so as to maintain the internal temperature of the reaction mixture below 5° C. The reaction mixture was allowed to warm to room temperature, then washed twice with water (100, then 150 ml). The combined aqueous washings were saturated with sodium chloride and exhaustively extracted with dichloromethane (×7), then the dichloromethane extracts and reaction solution were combined, dried ($Na_2SO_4$) and evaporated under reduced pressure. The residual solid was purified by column chromatography on silica gel, eluting with a solvent gradient of ethyl acetate:hexane (0:100 to 100:0), to provide the required amide as an oil. Rf 0.10 (SS 10) $\delta(CDCl_3)$: 2.88 (3H, d), 5.60 (1H, d), 5.95–6.30 (3H, m).

(b)

The title compound was prepared from the previous product (Example 64(a) and the title compound of Example 33 by a procedure similar to that described in Example 28(a), as a foam. Rf 0.40 (SS 7). $[\alpha]_D^{25}$+37° (c=0.1, $CH_3OH$). Found: C,70.81; H,8.81; N,10.17. $C_{24}H_{35}N_3O_2$; 0.14 $CH_2Cl_2$ requires C,70.71; H,8.68; N,10.26%.

EXAMPLE 65

5-(3-Hydroxy-3-methyl-1-but-1-enyl)-3-{N-[2-(N-methylcarbamoyl)ethyl]-2(R)-pyrrolidinylmethyl}-1H-indole (a) 5-Bromo-3-{N-[2-(N-methylcarbamoyl)ethyl]-2(R)-pyrrolidinylmethyl}-1H-indole Obtained from the products of Preparation 2 and Example 64(a), by a procedure similar to that described in Example 28(a), as a foam. Rf 0.54 (SS 7). $[\alpha]_D^{25}$+66° (c=0.1, $CH_3OH$). Found: C,55.53; H,5.96; N,11.42. $C_{17}H_{22}BrN_3O$ requires C,56.05; H,6.09; N,11.53%. LRMS: m/z 364.0 ($^{79}$Br M+1)$^+$ and 366.3 ($^{81}$Br M+1)$^+$.

(b)

The title compound was prepared from the previous product (Example 65(a)) by a procedure similar to that described in Example 1, using 2-methylbut-3-en-2-ol as the appropriate alkene, as a foam. Rf 0.18 (SS 7). $[\alpha]_D^{25}$+43° (c=0.1, $CH_3OH$). Found: C,67.85; H,8.56; N,10.20. $C_{22}H_{31}N_3O_2$; 0.33 $CH_2Cl_2$ requires C,67.81; H,8.06; N,10.63%.

EXAMPLE 66

5-(3-Hydroxy-3-methyl-1-butyl)-3-{N-[2-(N-methylcarbomoyl)ethyl]-2(R)-pyrrrolidinylmethyl}-1H-indole The title compound was obtained by either of the following methods.

(A)

Obtained from the title compound of Example 65 by using a procedure similar to that described in Example 2, but using 10% palladium on charcoal as catalyst at 30 p.s.i. (2.07 bar)

hydrogen pressure, as a foam. Rf 0.35 (SS 7). $[\alpha]_D^{25} 41°$ (c=0.1, CH$_3$OH). LRMS: m/z 372.2 (M+1)$^+$.

(B)

Obtained from the title compound of Example 29 and N-methylacrylamide (Example 64(a)), by a procedure similar to that described in Example 28(a), as a foam. Rf 0.05 (SS 13). $[\alpha]_D^{25}+58°$ (c=0.1, CH$_3$OH). Found: C,69.91; H,8.97; N,10.61. C$_{22}$H$_{33}$N$_3$O$_2$; 0.125 CH$_2$Cl$_2$ requires C,69.54; H,8.77; N,11.00%. LRMS: m/z 372.3 (M+1)$^+$.

EXAMPLE 67

5-(3-Hydroxy-3-methyl-1-but-1-enyl)-3-{N-[2-(N,N-dimethylcarbamoyl)ethyl]-2(R)-pyrrolidinylmethyl}-1H-indole Obtained from the product of Example 34(a) and 2-methylbut-3-en-2-ol, by a procedure similar to that described in Example 1, as a foam. Rf 0.37 (SS 7). $[\alpha]_D^{25}+21°$ (c=0.1, CH$_3$OH). Found: C,70.68; H,8.66; N,10.38. C$_{23}$H$_{33}$N$_3$O$_2$; 0.11 CH$_2$Cl$_2$ requires C,70.65; H,8.52; N,10.69%.

EXAMPLE 68

5-(3-Hydroxy-3-methyl-1-butyl)-3-{N-[2-(N,N-dimethylcarbamoyl)ethyl]-2(R)-pyrrolidinylmethyl}-1H-indole The title compound was obtained by either of the following methods.

(A)

Obtained from the title compound of Example 67 by a procedure similar to that described in Example 2, using 10% palladium on charcoal as a catalyst, as a foam. Rf 0.39 (SS 7). $[\alpha]_D^{25}+12°$ (c=0.1, CH$_3$OH). Found: C,68.09; H,9.21; N,10.38. C$_{23}$H$_{35}$N$_3$O$_2$; 0.10 CH$_2$Cl$_2$; 0.67 H$_2$O requires C,68.33; H,9.04; N,10.35%.

(B)

Obtained from the title compound of Example 29 and N,N-dimethylacrylamide, by a procedure similar to that described in Example 28(a), as a foam. $[\alpha]_D^{25}+41°$ (c=0.1, CH$_3$OH). Found: C,69.62; H,8.98; N,10.26. C$_{23}$H$_{35}$N$_3$O$_2$; 0.70 H$_2$O requires C,69.37; H,9.22; N,10.55%. LRMS: m/z 384.3 (M+1)$^+$.

EXAMPLE 69

3-{N-[2-(N,N-Dimethylcarbamoyl)ethyl]-2(R)-pyrrolidinylmethyl}-5-(3-oxo-1-but-1-enyl)-1H-indole Obtained from the product of Example 34(a) and methyl vinyl ketone, by a procedure similar to that described in Example 1, as a gum. Rf 0.50 (SS 7). $[\alpha]_D^{25}+42°$ (c=0.1, CH$_3$OH). Found: C,68.80; H,8.09; N,11.04. C$_{22}$H$_{29}$N$_3$O$_2$; 0.10 CH$_2$Cl$_2$; 0.50 H$_2$O requires C,68.95; H,7.91; N,10.92%.

EXAMPLE 70

3-{N-[2-(N,N-Dimethylcarbamoyl)ethyl]-2(R)-pyrrolidinylmethyl}-5-(3-oxo-1-butyl)-1H-indole Obtained from the title compound of Example 69 by a procedure similar to that described in Example 2, but using 10% palladium on charcoal as catalyst, as a gum. Rf 0.35 (SS 7). $[\alpha]_D^{25}+82°$ (c=0.1, CH$_3$OH). LRMS: m/z 370.6 (M+1)$^+$.

EXAMPLE 71

5-(3-Hydroxy-1-butyl)-3-{N-[2-(N,N-dimethylcarbamoyl)-ethyl]-2(R)-pyrrolidinylmethyl}-1H-indole Obtained from the title compound of Example 70, by a procedure similar to that described in Example 38, as a foam. Rf 0.28 (SS 7). $[\alpha]_D^{25}+51°$ (c=0.1, CH$_3$OH). Found: C,69.12; H,9.34; N,10.93. C$_{22}$H$_{33}$N$_3$O$_2$; 0.67 requires C,68.90; H,9.02; N,10.96%. LRMS: m/z 372.2 (M+1)$^+$.

EXAMPLE 72

5-(3-Hydroxy-3-methyl-1-butyl)-3-{N-[2-(N,N-dimethylcarbamoyl)-1-propyl]-2(R)-pyrrolidinylmethyl}-1H-indole A stirred solution of the title compound of Example 29 (400 mg, 1.4 mmol) and N,N-dimethylmethacrylamide (174 mg, 1.5 mmol) in pyridine (2 ml), under nitrogen, was heated under reflux for 61 hours, then a further quantity of N,N-dimethylmethacrylamide (315 mg, 2.8 mmol) was added to the reaction mixture. After a further 91 hours under reflux, the cool reaction mixture was diluted with ethyl acetate and then washed twice with 2M aqueous sodium carbonate solution. The combined aqueous washings were extracted with ethyl acetate, then the combined organic solutions dried (Na$_2$SO$_4$) and evaporated under reduced pressure. The residue was purified by column chromatography on silica gel, eluting with 0.880 aqueous ammonia:methanol: dichloromethane (0.5:5:95), to furnish the title compound as a single diastereoisomer. $[\alpha]_D^{25}+50°$ (c=0.1, CH$_3$OH). Found: C,70.59; H,9.02; N,9.94. C$_{24}$H$_{37}$N$_3$O$_2$; 0.15 CH$_2$Cl$_2$ requires C,70.35; H,9.12; N,10.19%. LRMS: m/z 400.3 (M+1)$^+$.

EXAMPLE 73

5-(3-Hydroxy-3-methyl-1-butyl)-3-{N-[2-(N-methylcarbamoyl)-1-propyl]-2(R)-pyrrolidinylmethyl}-1H-indole Obtained from the title compound of Example 29 and N-methylmethacrylamide, by a procedure similar to that described in Example 72, as a mixture of diastereoisomers which were separated by chromatography on silica gel, eluting with 0.880 aqueous ammonia: methanol:dichloromethane (0:1:5:95).

Diastereoisomer A

Foam. Rf 0.39 (SS 7). $[\alpha]_D^{25}+55°$ (c=0.1, CH$_3$OH). Found: C,68.97; H,9.04; .N,10.12. C$_{23}$H$_{35}$N$_3$O$_2$; 0.225 CH$_2$Cl$_2$ requires C,68.93; H,8.83; N,10.38%. LRMS: m/z 386.3 (M+1)$^+$.

Diastereoisomer B

Foam. Rf 0.32 (SS 7). $[\alpha]_D^{25}+6°$ (c=0.1, CH$_3$OH). Found: C,68.70; H,9.00; N,10.12. C$_{23}$H$_{35}$N$_3$O$_2$; 0.25 CH$_2$Cl$_2$ requires C,68.65; H,8.80; N,10.33%.

EXAMPLE 74

5-[2-(1-Hydroxycyclopentyl)ethyl]-3-[N-(2-morpholinocarbonylethyl))-2(R)-pyrrolidinylmethyl]-1H-indole Obtained from the title compound of Example 33 and N-acryloylmorpholine, by a procedure similar to that described in Example 28(a), as a foam. Rf 0.46 (SS 7).

$[\alpha]_D^{25}+24°$ (c=0.1, CH$_3$OH). Found: C,67.91; H,8.72; N,8.57. C$_{27}$H$_{39}$N$_3$O$_3$; 0.33 CH$_2$Cl$_2$; 0.10 H$_2$O requires C,68.17; H,8.34; N,8.73%. LRMS: m/z 454.3 (M+1)$^+$.

EXAMPLE 75

5-[2-(1-Hydroxycyclopentyl)ethyl]-3-{N-[2-(N-2-methoxyethylcarbomoyl)ethyl]-2(R)-pyrrolidinylmethyl}-1H-indole (a) N-(2-Methoxyethyl)acrylamide N,N-Diisopropylethylamine (3.21 g, 25 mmol) was added to a stirred, ice-cooled solution of acryloyl chloride (2.25 g, 25 mmol) in dichloromethane (30 ml) under nitrogen followed, 2 minutes later, by 2-methoxyethylamine (1.92 g, 25.6 mmol) added dropwise over 1 hour. The cooling bath was removed, then the reaction mixture stirred for 18 hours at room temperature and washed twice with water. The combined aqueous washings were saturated with sodium chloride and exhaustively extracted with dichloromethane. All the dichloromethane solutions were combined, washed twice with 2M aqueous sodium carbonate solution, dried (Na$_2$SO$_4$) and evaporated under reduced pressure. The residue was purified by column chromatography on silica gel, eluting with a solvent gradient of ethanol: dichloromethane (0:100 to 5:95), to yield the required amide as an oil. Rf 0.63 (SS 7). Found: C,54.97; H,9.24; N,10.68. C$_6$H$_{11}$NO$_2$; 0.10 H$_2$O requires C,55.04; H,8.62; N,10.70%. LRMS: m/z 130.4 (M+1)$^+$.

(b)

The title compound was obtained from the title compound of Example 33 and the previous product (Example 75(a)), by a procedure similar to that described in Example 28(a), as a foam. Rf 0.44 (SS 7). $[\alpha]_D^{25}+42°$ (c=0.1, CH$_3$OH). Found: C,68.59; H,9.02; N,9.11. C$_{26}$H$_{39}$N$_3$O$_3$; H$_2$O requires C,68.61; H,8.96; N,9.23%. LRMS: m/z 442.4 (M+1)$^+$.

EXAMPLE 76

3-{N-[2-(N-2-Benzyloxyethylcarbamoyl)ethyl]-2(R)-pyrrolidinylmethyl}-5-[2-(1-hydroxycyclopentyl)ethyl]-1H-indole (a) N-(2-Benzyloxyethyl)acetamide A solution of N-acetylethanolamine (10.0 g, 6.79 ml, 97 mmol) in a mixture of anhydrous tetrahydrofuran (100 ml) and dimethylformamide (10 ml) was added to a stirred suspension of 80% sodium hydride in oil dispersion (2.90 g, 97 mmol) in dry tetrahydrofuran (140 ml), under nitrogen, at room temperature. After 1 hour, the reaction mixture was heated to 40°–50° C. and then, after a further 0.5 hour, cooled to ice-bath temperature. Next, benzyl bromide (13.8 ml, 116 mmol) was added and the resulting suspension stirred at room temperature for 18 hours, before being cautiously quenched with water (400 ml). The resulting mixture was extracted with ethyl acetate (2×300 ml) and the combined extracts washed with water (200 ml), dried (Na$_2$SO$_4$) and evaporated under reduced pressure. The resulting residue was partitioned between ethyl acetate and water, then the organic phase washed thrice with water, dried (Na$_2$SO$_4$) and evaporated under reduced pressure. The crude product was purified by column chromatography on silica gel, eluting with a solvent gradient of methanol:ethyl acetate (0:100 to 10:90), to give the required product (7.8 g) as an oil. Rf 0.21 (SS 17). LRMS: m/z 194.3 (M+1)$^+$.

(b) 2-Benzyloxyethylamine

6M Hydrochloric acid (60 ml) was added to a stirred solution of the previous product (Example 76(a); 7.80 g, 40 mmol) in methanol (125 ml) and the resulting mixture heated under reflux for 48 hours, then evaporated under reduced pressure. The residue was partitioned between ethyl acetate and water, and the pH of the separated aqueous phase adjusted to neutrality with 2M aqueous sodium hydroxide solution. The aqueous phase was exhaustively extracted with ethyl acetate and the combined extracts dried (Na$_2$SO$_4$) and evaporated under reduced pressure to provide the required amine as an oil. Rf 0.16 (SS 7). LRMS: m/z 152.4 (M+1)$^+$.

(c) N-Acryloyl-2-benzyloxyethylamine

Obtained from the previous product (Example 76(b)) and acryloyl chloride, by a procedure similar to that described in Example 75(a), as an oil. Rf 0.68 (SS 7). Found: C,68.94; H,7.13; N,6.42. C$_{12}$H$_{15}$NO$_2$; 0.06 CH$_2$Cl$_2$ requires C,68.83; H,7.24; N,6.65%. LRMS: m/z 206.1 (M+1)$^+$.

(d)

The title compound was obtained from the title compound of Example 33 and the previous product (Example 76(c)), by a procedure similar to that described in Example 28(a), as a foam. Rf 0.42 (SS 7). $[\alpha]_D^{25}+30°$ (c=0.1, CH$_3$OH). Found: C,73.23; H,8.36; N,7.99. C$_{32}$H$_{43}$N$_3$O; 0.10 CH$_2$Cl$_2$ requires C,73.26; H,8.27; N,7.98%. LRMS: m/z 519.0 (M+1)$^+$.

EXAMPLE 77

5-[2-(1-Hydroxycyclopentyl)ethyl]-3-{N-[2-(N-2-hydroxyethylcarbamoyl)ethyl]-2(R)-pyrrolidinylmethyl}-1H-indole Obtained from the title compound of Example 76 by a procedure similar to that described in Example 2, but using 10% palladium on charcoal as a catalyst, as a foam. Rf 0.19 (SS 7). $[\alpha]_D^{25}+41°$ (c=0.1, CH$_3$OH). Found: C,67.50; H,8.40; N,8.96. C$_{25}$H$_{37}$N$_3$O$_3$; 0.17 CH$_2$Cl$_2$ requires C,67.05; H,8.46; N,9.32%. LRMS: m/z 428.8 (M+1)$^+$.

EXAMPLE 78

5-[2-(1-Hydroxycyclopentyl)ethyl]-3-{N-[2-(N,N-dimethylcarbamoylmethyl]carbamoyl)ethyl]-2(R)-pyrrolidinylmethyl}-1H-indole (a) N-Benzyloxycarbonylglycine dimethylamide Obtained from N-benzyloxycarbonylglycine and dimethylamine hydrochloride, by a "peptide coupling procedure" similar to that described in Example 81(b), as an oil. Rf 0.35 (SS 20). Found: C,60.76; H,6.93; N,11.62. C$_{12}$H$_{16}$N$_2$O$_3$ requires C,61.00; H,6.83; N,11.86%. LRMS: m/z 237.0 (M+1)$^+$.

(b) Glycine dimethylamide

Obtained from the previous product (Example 78(a)) by a procedure similar to that described in Example 2, but using 10% palladium on charcoal as catalyst, as an oil. Rf 0.21 (SS 7). LRMS: m/z 103.1 (M+1)$^+$. HRMS: m/z 103.08710.

(c) N-Acryloylglycine dimethylamide

Obtained from the previous product (Example 78(b)) and acryloyl chloride, by a procedure similar to that described in Example 75(a), as a solid, m.p. 74°–75° C. Rf 0.61 (SS 7). Found: C,53.84; H,7.86; N,17.58. C$_7$H$_{12}$N$_2$O$_2$ requires C,53.83; H,7.74; N,17.94%. LRMS: m/z 157.2 (M+1)$^+$.

(d)

The title compound was obtained from the previous product (Example 78(c)) and the title compound of Example 33, by a procedure similar to that described in Example 28(a), as a foam. Rf 0.21 (SS 7). $[\alpha]_D^{25}+40°$ (c=0.1, CH$_3$OH). Found: C,65.44; H,8.42; N,10.78. C$_{27}$H$_{40}$N$_4$O$_3$; 0.33 CH$_2$Cl$_2$; 0.50 H$_2$O requires C,65.16; H,8.33; N,11.13%. LRMS: m/z 469.7 (M+1)$^+$.

EXAMPLE 79

5-[2-(1-Hydroxycyclopentyl)ethyl]-3-{N-[2-(N-[2-(N,N-dimethylcarbomoyl)ethyl]carbamoyl)ethyl]-2(R)-pyrrolidinylmethyl}-1H-indole (a) N-Benzyloxycarbonyl-B-alanine dimethylamide Obtained from N-benzyloxycarbonyl-B-alanine and dimethylamine hydrochloride, by a procedure similar to that described in Example 81 (b), as an oil. Rf 0.51 (SS 7). LRMS: m/z 251.3 (M+1)$^+$.

(b) B-Alanine dimethylamide

Obtained from the previous product (Example 79(a)) by a procedure similar to that described in Example 2, but using 10% palladium on charcoal as catalyst, as an oil. Rf 0.10 (SS 7). LRMS: m/z 117.0 (M+1)$^+$.

(c) N-Acryloyl-B-alanine dimethylamide

Obtained from the previous product (Example 79(b)) and acryloyl chloride, by a procedure similar to that described in Example 75(a), as a solid, m.p. 79°–80.5° C. Rf 0.46 (SS 7). Found: C,55.42; H,8.29; N,16.04. C$_8$H$_{14}$N$_2$O$_2$; 0.20 H$_2$O requires C,55.28; H,8.35; N,16.12%. LRMS: m/z 171.4 (M+1)$^+$.

(d)

The title compound was obtained from the previous product (Example 79(c)). and the title compound of Example 33, by a procedure similar to that described in Example 28(a), as a foam. Rf 0.16 (SS 7). $[\alpha]_D^{25}+44°$ (c=0.1, CH$_3$OH). Found: C,67.35; H,8.35; N,11.00. C$_{28}$H$_{42}$N$_4$O$_3$; 0.33 CH$_2$Cl$_2$ requires C,67.74; H,8.45; N,11.03%. LRMS: m/z 483.2 (M+1)$^+$.

EXAMPLE 80

3-[N-(3-Benzyloxycarbonyl-1-propyl)-2(R)-pyrrolidinylmethyl]-5-[2-(1-hydroxycyclopentyl)ethyl]-1H-indole (a) Benzyl 4-bromobutanoate 80% Sodium hydride dispersion in oil (0.18 g, 5.9 mmol) was added portionwise to a stirred solution of benzyl alcohol (0.64 g, 5.9 mmol) in anhydrous tetrahydrofuran (10 ml) under nitrogen. After a further 1 hour at room temperature, the reaction mixture was cooled to −70° C. and a solution of 4-bromobutanoyl chloride (1.0 g, 5.4 mmol) in anhydrous tetrahydrofuran (3 ml) added dropwise. After 0.5 hour, the cooling bath was removed and the reaction mixture quenched at room temperature with 5% aqueous ammonium chloride solution (20 ml) and then extracted with dichloromethane (3×20 ml). The combined extracts were washed with saturated brine, dried (Na$_2$SO$_4$) and evaporated under reduced pressure, then the residue was purified by column chromatography on silica gel, eluting with dichloromethane, to give the required ester as a gum. Rf 0.60 (SS 16).

(b)

The title compound was obtained from the previous product (Example 80(a)) and the title compound of Example 33, by a procedure similar to that described in Example 24(A)(a), as a gum. Rf 0.50 (SS 7). $[\alpha]_D^{25}+8°$ (c=0.1, CH$_3$OH). Found: C,74.62; H,8.11; N,5.43. C$_{31}$H$_{42}$N$_2$O$_3$; 0.83 CH$_2$Cl$_2$; 0.25 H$_2$O requires C,74.63; H,8.19; N,5.60%.

EXAMPLE 81

5-[2-(1-Hydroxycyclopentyl)ethyl]-3-{N-[3-(N-methylcarbamoyl)-1)-1-propyl]-2(R)-pyrrolidinylmethyl}-1H-indole (a) 5-[2-(1-Hydroxycyclopentyl)ethyl]-3-[N-(3-carboxy-1-propyl)-2(R)-pyrrolidinylmethyl]-1H-indole Obtained from the title compound of Example 80 by a procedure similar to that described in Example 2, but using 10% palladium on charcoal as catalyst, as a foam. Rf 0.15 (SS 7). $[\alpha]_D^{25}-49°$ (c=0.1, CH$_3$OH). Found: C,66.41; H,8.43; N,6.38. C$_{24}$H$_{34}$N$_2$O$_3$; 0.50 CH$_2$Cl$_2$ requires C,66.72; H,8.00; N,6.35%. LRMS: m/z 381.2 (M+1–H$_2$O)$^+$.

(b)

A solution of the previous product (Example 81(a) 200 mg, 0.5 mmol), methylamine hydrochloride (37 mg, 0.55 mmol), 1-hydroxybenzotriazole (68 mg, 0.5 mmol), 1-ethyl-3-dimethylaminopropylcarbodiimide hydrochloride (125 mg, 0.65 mmol) and N-methylmorphoiine (0.19 ml, 1.7 mmol) in dichloromethane (10 ml) was stirred under nitrogen at 0°–5° C. for 1 hour and then at room temperature for 24 hours. The reaction mixture was again cooled using an ice bath and further quantities of 1-hydroxybenzotriazole (68 mg, 0.5 mmol), 1-ethyl-3dimethylaminopropylcarbodiimide hydrochloride (100 mg, 0.52 mmol) and N-methylmorpholine (0.2 ml) added. After a further 0.5 hour, a further quantity of methylamine hydrochloride (100 mg, 1.5 mmol) was added, and stirring at 0°–5° C. continued for 2 hours and then at room temperature for a further 70 hours. The resulting reaction mixture was washed with water and saturated brine, dried (Na$_2$SO$_4$) and evaporated under reduced pressure, then the residue purified by column chromatography on silica gel, eluting initially with dichloromethane and then with a solvent gradient of 0.880 aqueous ammonia:methanol:dichloromethane (0:10:90 to 1:10:90 to 2:20:80), to afford the title compound as a foam. Rf 0.15 (SS 7). $[\alpha]_D^{25}+22°$ (c=0.1, CH$_3$OH).

Found: C,68.66; H,8.54; N,9.61. C$_{25}$H$_{37}$N$_3$O$_2$; 0.17 CH$_2$Cl$_2$; 0.75 H$_2$O requires C,68.81; H,8.91; N,9.58 %. LRMS: m/z 412.7 (M+1)$^+$.

EXAMPLE 82

5-[2-(1-Hydroxycyclopentyl)ethyl]-3-{N-[4-(N-methylcarbamoyl)-1-butyl]-2(R)-pyrrolidinylmethyl}-1H-indole (a) N-Methyl-5-bromopentanamide Obtained from 5-bromopentanoic acid and methylamine hydrochloride, by a procedure similar to that described in Example 81(b), as an oil. Rf 0.35 (SS 17). Found: C,36.61; H,6.58; N,6.82. C$_6$H$_{12}$BrNo requires C,37.13; H,6.23; N,7.22%.

(b)

The title compound was obtained from the previous product (Example 82(a)) and the title compound of Example 33, by a procedure similar to that described in Example 24(A)(a), as a foam. Rf 0.15 (SS 7). $[\alpha]_D^{25}+41°$ (c=0.1, CH$_3$OH). Found: C,71.18; H,9.23; N,9.57. C$_{26}$H$_{39}$N$_3$O$_2$; 0.67 H$_2$O requires C,71.35; H,9.29; N,9.60%. LRMS: m/z 425.8 (M)$^+$.

EXAMPLE 83

5-[2-(1-Hydroxycyclopentyl)ethyl]-3-{N-[5-(N-methylcarbamoyl)-1-pentyl]-2(R)-pyrrolidinylmethyl}-1H-indole (a) N-Methyl-6-iodohexanamide Obtained from 6-iodohexanoic acid and methylamine hydrochloride, by a procedure similar to that described in Example 81(b), as a foam. Rf 0.30 (SS 17). Found: C,33.84; H,5.47; N,5.35. $C_7H_{14}INO$; 0.10 $CH_3CO_2CH_2CH_3$ requires C,33.67; H,5.65; N,5.31%. LRMS: m/z 256.1 $(M+1)^+$.

(b)

The title compound was obtained from the previous product (Example 83(a)) and the title compound of Example 33, by a procedure similar to that described in Example 24(A)(a), as a foam. Rf 0.10 (SS 7). $[\alpha]_D^{25}+32°$ (c=0.1, $CH_3OH$). Found: C,71.31; H,9.82; N,9.24. $C_{27}H_{41}N_3O_2$; 0.75 $H_2O$ requires C,71.56; H,9.45; N,9.27%. LRMS: m/z 440.4 $(M+1)^+$.

EXAMPLE 84

5-(3-Hydroxy-3-methyl-1-butyl]-3-{N-[5-(N-methylcarbamoyl)-1-pentyl]-2(R)-pyrrolidinylmethyl}-1H-indole Obtained from the product of Example 83(a) and the title compound of Example 29, by a procedure similar to that described in Example 24(A)(a), as a foam. Rf 0.30 (SS 7). $[\alpha]_D^{25}+51°$ (c=0.1, $CH_3OH$). Found: C,69.12; H,9.76; N,9.53. $C_{25}H_{39}N_3O_2$; 0.10 $CH_2Cl_2$; 0.75 $H_2O$ requires C,69.21; H,9.42; N,9.65%. LRMS: m/z 414.6 $(M+1)^+$.

EXAMPLE 85

5-[2-(1-Hydroxycyclopentyl)ethyl]-3-[N-(2-sulphamoylethyl)-2(R)-pyrrolidinylmethyl]-1H-indole Obtained from the title compound of Example 33 and vinylsulphonamide by a procedure similar to that described in Example 28(a), but using dimethylformamide as solvent, as a foam. Rf 0.40 (SS 7). $[\alpha]_D^{25}+49°$ (c=0.1, $CH_3OH$). Found: C,61.38; H,8.16; N,9.60. $C_{22}H_{33}N_3O_3S$; 0.17 $CH_2Cl_2$ requires C,61.38; H,7.75; N,9.69%. LRMS: m/z 420.1 $(M+1)^+$.

EXAMPLE 86

5-[2-(1-Hydroxycyclopentyl)ethyl]-3-{N-[2-(N-methylsulphamoyl)ethyl]-2(R)-pyrrolidinylmethyl}-1H-indole Obtained from the title compound of Example 33 and N-methylvinylsulphonamide (WO-A-92/06973), by a procedure similar to that described in Example 28(a), as a foam. Rf 0.49 (SS 7). $[\alpha]_D^{25}+38°$ (c=0.1, $CH_3OH$). Found: C,62.47; H,8.11, N,9.29. $C_{23}H_{35}N_3O_3S$; 0.05 $CH_2Cl_2$; 0.25 $H_2O$ requires C,62.57; H,8.11; N,9.49%. LRMS: m/z 434.7 $(M+1)^+$.

EXAMPLE 87

5-[2-(1-Hydroxycyclopentyl)ethyl]-3-{N-[2-(N,N,-dimethylsulphamoyl)ethyl]-2(R)-pyrrolidinylmethyl}-1H-indole Obtained from the title compound of Example 33 and N,N-dimethylvinylsulphonamide (WO-A-92/06973), by a procedure similar to that described in Example 28(a), as a solid, m.p. 118.5°–119.5° C. Rf 0.91 (SS 7). $[\alpha]_D^{25}+31°$ (c=0.1, $CH_3OH$). Found: C,64.03; H,8.57; N,9.30. $C_{24}H_{37}N_3O_3S$ requires C,64.39; H,8.33; N,9.39%. LRMS: m/z 448.3 $(M+1)^+$.

EXAMPLE 88

3-[N-(2-Aminoethyl)-2(R)-pyrrolidinylmethyl]-5-[2-(1-hydroxycyclopentyl)ethyl]-1H-indole (a) 5-[2-(1-Hydroxycyclopentyl)ethyl]-3-[N-(2-phthalimidoethyl)-2(R)-pyrrolidinylmethyl]-1H-indole Obtained from the title compound of Example 33 and N-(2-bromoethyl)phthalimide by a procedure similar to that described in Example 24(A)(a), but using anhydrous potassium carbonate as base and acetonitrile as solvent, as a foam. Rf 0.48 (SS 7). $[\alpha]_D^{25}+25°$ (c=0.1, $CH_3OH$). Found: C,69.10; H,6.75; N,7.47. $C_{30}H_{35}N_3O_3$; 0.50 $CH_2Cl_2$; 0.10 $H_2O$ requires C,69.12; H,6.88; N,7.93%. LRMS: m/z 486.3 $(M+1)^+$.

(b)

The title compound was obtained from the previous product (Example 88(a)) and hydrazine hydrate, by a procedure similar to that described in Example 47(b), as a foam. Rf 0.19 (SS 4). $[\alpha]_D^{25}+48°$ (c=0.1, $CH_3OH$). Found: C,72.42; H,9.07; N,11.14. $C_{22}H_{33}N_3O$; 0.03 $CH_2Cl_2$; 0.50 $H_2O$ requires C,72.11; H,9.35; N,11.45%. LRMS: m/z 356.5 $(M+1)^+$.

EXAMPLE 89

3-[N-(2-Acetamidoethyl)-2(R)-pyrrolidinylmethyl]-5-[2(1-hydroxycyclopentyl)ethyl]-1H-indole Triethylamine (86 µl, 0.62 mmol) and then acetic acid anhydride (58 µl, 0.62 mmol) were added to a stirred solution of the title compound of Example 88 (200 mg, 0.56 mmol) in dichloromethane (10 ml) at −40° C. under nitrogen. The cooling bath was removed and, after 2 hours, the reaction mixture was partitioned between dichloromethane and water. The organic phase was washed with water, dried ($Na_2SO_4$) and evaporated under reduced pressure to give a foam which was purified by column chromatography on silica gel, eluting initially with dichloromethane and then with a solvent gradient of 0.880 aqueous ammonia:methanol:dichloromethane (0:5:95 to 1:10:90), to yield the title compound (180 mg) as a foam. Rf 0.19 (SS 7). $[\alpha]_D^{25}+46°$ (c=0.1, $CH_3OH$). Found: C,70.59; H,8.94; N,10.40. $C_{24}H_{35}N_3O_2$; 0.10 $CH_2Cl_2$; 0.50 $H_2O$ requires C,70.87; H,8.93; N,10.29%. LRMS: m/z 397.9 $(M+1)^+$.

EXAMPLE 90

5-[2-(1-Hydroxycyclopentyl)ethyl]-3-[N-(2-methanesulphonamidoethyl)-2(R)-pyrrolidinylmethyl]-1H-indole Obtained from the title compound of Example 88 by a procedure similar to that described in Example 89, but using methanesulphonyl chloride as the electrophile, an addition temperature of −78° C. and subsequent stirring at room temperature for 18 hours, as a foam. Found: C,59.88; H,7.87; N,9.51. $C_{23}H_{35}N_3O_3S$; 0.25 $CH_2Cl_2$; 0.50 $H_2O$ requires C,60.19; H,7.92; N,9.06%. LRMS: m/z 433.7 $(M+1)^+$.

EXAMPLE 91

5-[2-(1-Hydroxycyclopentyl)ethyl]-3-[N-(2-sulphamidoethyl)-2(R)-pyrrolidinylmethyl]-1H-indole A stirred solution of the title compound of Example 88 (200 mg, 0.56 mmol) and sulphamide (270 mg, 2.8 mmol) in 1,4-dioxane (5 ml), under nitrogen, was heated under reflux for 1.5 hours. The solvent was removed by evaporation under reduced pressure and the residue partitioned between dichloromethane and water. The organic phase was dried ($Na_2SO_4$) and evaporated under reduced pressure to give an oil which was purified by column chromatography on silica gel, eluting initially with dichloromethane and then with a solvent gradient of 0.880 aqueous ammonia:methanol:dichloromethane (0:1:99 to 1:10:90), to furnish the title compound as a foam. Rf 0.25 (SS 7). $[\alpha]_D^{25}$+57° (c=0.1, $CH_3OH$). Found: C,60.43; H,7.91; N,11.75. $C_{22}H_{34}N_4O_3S$; 0.40 $CH_3CH_2OH$ requires C,60.44; H,8.09; N,12.37%. LRMS: m/z 435.4$(M+1)^+$.

EXAMPLE 92

5-(3-Hydroxy-3,4-dimethyl-1-pentyl)-3-(2(R)-pyrrolidinylmethyl)-1H-indole (a) 3,4-Dimethylpent-1-en-3-ol Obtained by a procedure similar to that described in Example 5(a), using 3-methylbutan-2-one as the appropriate ketone, as an oil. The crude product was purified by column chromatography on silica gel, eluting with n-pentane, to afford the required alcohol as a 1:1 mixture with n-pentane which was used as such in the next step. Rf 0.50 (SS 10). $\delta(CDCl_3)$: 0.82–1.00 (12H, m), 1.15–1.38 (9H, m), 1.65–1.90 (1H, m), 5.08–5.25 (2H, dd), 5.88–5.98 (1H, dd).

(b) 3-(N-Benzyloxycarbonyl-2(R)-pyrrolidinylmethyl)-5(3-hydroxy-3,4-dimethyl-1-pent-1-enyl)-1H-indole Obtained from the previous product (Example 92(a)) and the title compound of Preparation 1, by a procedure similar to that described in Example 1, as a foam. Rf 0.70 (SS 7). Found: C,74.96; H,7.48; N,6.01. $C_{28}H_{34}N_2O_3$; 0.05 $CH_2Cl_2$ requires C,74.73; H,7.62; N,6.21%.

(c)

The title compound was obtained from the previous product (Example 92(b)) by a procedure similar to that described in Example 2, but using 10% palladium on charcoal as catalyst, as a foam. Rf 0.10 (SS 7). $[\alpha]_D^{25}$−19° (c=0.1, $CH_3OH$). Found: C,73.66; H,9.52; N,8.32. $C_{20}H_{30}N_2O$; 0.10 $CH_2Cl_2$; 0.25 $H_2O$ requires C,73.72; H,9.45; N,8.56%. LRMS: m/z 315.3 $(M+1)^+$.

EXAMPLE 93

5-(3-Cyclopentyl-3-oxo-1-propyl)-3-(2(R)-pyrrolidinylmethyl)-1H-indole (a) N-Cyclopentanecarbonyl-N,O-dimethylhydroxylamine Oxalyl chloride (7.5 ml, 85 mmol) was added dropwise to a stirred solution of cyclopentanecarboxylic acid (4.56 g, 40 mmol) and dimethylformamide (2 drops) in dichloromethane (20 ml) under nitrogen at room temperature. After 2 hours, the reaction mixture was evaporated under reduced pressure and the residual oxalyl chloride removed azeotropically using dichloromethane. The resulting oil was dissolved in dichloromethane (50 ml) and N,O-dimethylhydroxylamine (4.3 g, 44 mmol) added portionwise to the stirred solution. The resulting mixture was cooled using an ice bath, pyridine (7.1 ml, 88 mmol) added, the cooling bath removed and stirring continued for 18 hours. The reaction mixture was then diluted with dichloromethane (50 ml), washed with 5% aqueous citric acid solution (×2) and saturated brine, dried ($Na_2SO_4$) and evaporated under reduced pressure. The residue was purified by chromatography on silica gel, eluting with a solvent gradient of methanol:dichloromethane (0:100 to 2:98), to furnish the required amide as an oil. Rf 0.50 (SS 18). Found: C,59.28; H,9.74; N,8.81. $C_8H_{15}NO_2$; 0.25 $H_2O$ requires C,59.41; H,9.66; N,8.66%.

(b) Cyclopentyl vinyl ketone

Obtained (with dichloromethane as solrate) from the previous product (Example 93(a)) and vinylmagnesium bromide, using a procedure similar to that described in Example 5(a), as an oil. Rf 0.60 (SS 16).

(c) 3-(N-Benzyloxycarbonyl-2(R)-pyrrolidinylmethyl)-5-(3-cyclopentyl-1-prop-1-enyl)-1H-indole Obtained from the previous product (Example 93(b)) and the title compound of Preparation 1, using a procedure similar to that described in Example 1, as a foam. Rf 0.50 (SS 19). $[\alpha]_D^{25}$−44° (c=0.1, $CH_3OH$). Found: C,75.18; H,7.06;.N,5.83. $C_{29}H_{32}N_2O_3$; 0.10 $CH_2Cl_2$ requires C,75.15; H,6.98; N,6.02%. LRMS: m/z 457.2 $(M+1)^+$.

(d)

The title compound was obtained. from the previous product (Example 93(c)) by a procedure similar to that described in Example 2, but using 10% palladium on charcoal as catalyst, as a foam. Rf 0.20 (SS 7). Found: C,74.65; H,8.40; N,8.20. $C_{21}H_{28}N_2O$; 0.20 $CH_2Cl_2$ requires C,74.57; H,8.38; N,8.21%. LRMS: m/z 325.2 $(M+1)^+$.

EXAMPLE 94

5-(3-Cyclopentyl-3-hydroxy-1-propyl)-3-(2(R)-pyrrolidinylmethyl)-1H-indole

The title compound was obtained from the title compound of Example 93, by a procedure similar to that described in Example 38, as a foam. Rf 0.10 (SS 7). $[\alpha]_D^{25}$−19° (c=0.1, $CH_3OH$). Found: C,74.71; H,9.21; N,8.33. $C_{21}H_{30}N_2O$; 0.67 $H_2O$ requires C,74.51; H,9.33; N,8.38%. LRMS: m/z 327.3 $(M+1)^+$.

EXAMPLE 95

5-(3-Hydroxy-3-trifluoromethyl-1-butyl)-3-(2(R)-pyrrolidinylmethyl)-1H-indole (a) 2-Trifluoromethylbut-3-en-2-ol Obtained (with tetrahydrofuran as solvate) from 1,1,1-trifluoroacetone and vinylmagnesium bromide, using a procedure similar to that described in Example 5(a), as an oil (product:tetrahydrofuran (30:70)). $\delta(CDCl_3)$: 1.42 (3H, s), 1.78–1.95 (4.7H, m), 2.42 (1H, s), 3.65–3.80 (4.7H, m), 5.38 (1H, d), 5.55 (1H, d), 5.95–6.18 (1H, dd).

(b) 3-N-(Benzyloxycarbonyl-2(R)-pyrrolidinylmethyl)-5(3-hydroxy-3-trifluoromethyl-1-but-1-enyl)-1H-indole Obtained from the previous product (Example 95(a)) and the title compound of Preparation 1, using a procedure similar to that described in Example 1, as a foam. Rf 0.75 (SS 7). $[\alpha]_D^{25}$ –14° (c=0.1, $CH_3OH$). Found: C,64.36; H,5.65; N,5.59. $C_{26}H_{27}F_3N_2O_3$; 0.10 $CH_2Cl_2$ requires C,64.37; H,5.77; N,5.75%.

(c)

The title compound was obtained from the previous product (Example 95(b)) by a procedure similar to that described in Example 2, but using 10% palladium on charcoal as catalyst, as a foam. Rf 0.08 (SS 7). $[\alpha]_D^{25}$ –24° (c=0.1, $CH_3OH$). Found: C,61.46; H,6.48; N,7.83. $C_{18}H_{23}F_3N_2O$; 0.10 $CH_2Cl_2$; 0.25 $H_2O$ requires C,61.52; H,6.76; N,7.93%. LRMS: m/z 341.2 $(M+1)^+$.

EXAMPLE 96

5-(3-Hydroxy-3-trifluoromethyl-1-but-1-enyl)-3-(N-methyl-2(R)-pyrrolidinylmethyl)-1H-indole Obtained from the product of Example 95(a) and 5-bromo-3-(N-methyl-2(R)-pyrrolidinylmethyl)-1H-indole (WO-A-92/06973), by a procedure similar to that described in Example 1, as a foam. Rf 0.15 (SS 7). Found: C,60.50; H,6.61; N,7.61. $C_{19}H_{23}F_3N_2O$; 0.125 $CH_2Cl_2$ requires C,60.29; H,6.68; N,7.35%. LRMS: m/z 353.2 $(M+1)^+$.

EXAMPLE 97

5-(3-Hydroxy-3-trifluoromethyl-1-butyl)-3-(N-methyl-2(R)-pyrrolidinylmethyl)-1H-indole Obtained from the title compound of Example 96 by a procedure similar to that described in Example 2, but using 10% palladium on charcoal as catalyst, as a foam. Rf 0.40 (SS 7). Found: C,59.55; H,6.86; N,7.10. $C_{19}H_{25}F_3N_2O$; 0.17 $CH_2Cl_2$; $H_2O$ requires C,59.55; H,7.13; N,7.25%. LRMS: m/z 355.0 $(M+1)^+$.

EXAMPLE 98

5-(3-Hydroxy-3-trifluoromethyl-1-but-1-enyl)-3-{N-[2-(N-methylcarbamoyl)ethyl]-2(R)-pyrrolidinylmethyl}-1H-indole Obtained from the products of Example 95(a) and Example 65(a), by a procedure similar to that described in Example 1, as a foam. Rf 0.15 (SS 7). Found: C,60.51; H,6.81; N,9.34. $C_{22}H_{28}F_3N_3O_2$; 0.10 $CH_2Cl_2$; 0.50 $H_2O$ requires C,60.19; H,6.67; N,9.53%. LRMS: m/z 424.5 $(M+1)^+$.

EXAMPLE 99

5-(3-Hydroxy-3-trifluoromethyl-1-butyl)-3-{N-[2-(N-methylcarbamoyl)ethyl]2(R)-pyrrolidinylmethyl}-1H-indole Obtained from the title compound of Example 98 by a procedure similar to that described in Example 2, but using 10% palladium on charcoal as catalyst, as a foam. Rf 0.45 (SS 7). $[\alpha]_D^{25}$ +39° (c=0.1, $CH_3OH$). Found: C,59.07; H,7.16; N,9.21. $C_{22}H_{30}F_3N_3O_2$; 0.05 $CH_2Cl_2$; $H_2O$ requires C,59.15; H,7.22; N,9.39%. LRMS: m/z 426.4 $(M+1)^+$.

EXAMPLE 100

5-[2-(3-Hydroxy-3-tetrahydrofuranyl)ethenyl]-3-{N-[2-(N,N-dimethylcarbamoyl)ethyl]-2(R)-pyrrolidinylmethyl}-1H-indole (a) 3-Hydroxy-3-vinyltetrahydrofuran Obtained from tetrahydrofuran-3-one (J. Org. Chem., 1989, 54, 1249) and vinylmagnesium bromide, by a procedure similar to that described in Example 5(a), as an oil. Rf 0.45 (SS 7). $\delta(CDCl_3)$: 1.90 (1H, br s), 1.92–2.20 (2H, m), 3.62–3.78 (2H, m), 3.92–4.10 (2H, m), 5.20 (1H, d), 5.44 (1H, d), 5.95–6.08 (1H, dd). HRMS: m/z 114.068.

(b)

The title compound was obtained from the previous product (Example 100(a)) and the product of Example 34(a), by a procedure similar to that described in Example 1, as a foam. Rf 0.26 (SS 7). $[\alpha]_D^{25}$ +33° (c=0.1, $CH_3OH$). Found: C,64.18; H,7.92; N,9.06. $C_{24}H_{33}N_3O_3$; 0.05 $CH_2Cl_2$; 0.10 $H_2O$ requires C,64.08; H,7.51; N,9.13%. LRMS: m/z 412.0 $(M+1)^+$.

EXAMPLE 101

5-[2-(3-Hydroxy-3-tetrahydrofuranyl)ethyl]-3-{N-[2-(N,N-dimethylcarbamoyl)ethyl]-2(R)-pyrrolidinylmethyl}-1H-indole Obtained from the title compound of Example 100 by a procedure similar to that described in Example 2, but using 10% palladium on charcoal as catalyst, as a foam. Rf 0.16 (SS 7). $[\alpha]_D^{25}$ +42° (c=0.1, $CH_3OH$). Found: C,67.20; H,9.18; N,9.41. $C_{24}H_{35}N_3O_3$; 0.10 $CH_3CH_2OH$; 0.90 $H_2O$ requires C,66.91; H,8.67; N,9.67%. LRMS: m/z 414.47 $(M+1)^+$.

EXAMPLE 102

5-(3-Hydroxy-3-methyl-1-butyl)-3-(N-methyl-4-piperidyl-1H-indole

Obtained from the title compound of Example 46 by a procedure similar to that described in Example 2, but using 10% palladium on charcoal as catalyst, as a solid, m.p. 144°–145° C. Rf 0.32 (SS 7). Found: C,74.57; H,9.61; N,8.98. $C_{19}H_{28}N_2O$; 0.12 $CH_3CH_2OH$ requires C,74.68; H,9.46; N,9.16%. LRMS: m/z 301.2 $(M+1)^+$.

EXAMPLE 103

5-[2-(1-Hydroxycyclopentl)ethyl]-3-[4-(1,2,5,6-tetrahvdropyridyl)]-1H-indole (a) 5- [2-(1-Hydroxycyclopentyl)ethenyl]-1H-indole Obtained from the product of Example 5(a) and 5-bromoindole, by a procedure similar to that described in Example 1, as a solid. Rf 0.57 (SS 7). Found: C,78.42; H,7.24; N,5.51. $C_{15}H_{17}NO$; 0.13 $H_2O$ requires C,78.41; H,7.58; N,6.09%. LRMS: m/z 210.1 $(M+1-H_2O)^+$.

(b) 5-[2-(1-Hydroycyclopentyl)ethyl]-1H-indole

Obtained from the previous product (Example 103(a)) by a procedure similar to that described in Example 2, but using 10% palladium on charcoal as catalyst and a 1:10 mixture of N,N-dimethylacetamide:ethanol as solvent, as a solid, m.p. 117°–118° C. Rf 0.67 (SS 7). Found: C,77.93; H,8.44; N,5.58. $C_{15}H_{19}NO$; 0.10 $H_2O$ requires C,77.95; H,8.37; N,6.06%. LRMS: m/z 212 $(M+1-H_2O)^+$.

(c)

Potassium hydroxide (53.9 mg, 0.96 mmol) was added to a stirred solution of the previous product (Example 103(b); 200 mg, 0.87 mmol) and 4-piperidone monohydrate hydrochloride (148 mg, 0.096 mmol) in methanol (10 ml) under nitrogen and the resulting mixture heated under reflux for 48 hours. The cool reaction mixture was poured into water (50 ml) and the resulting solid collected, washed with water and dried in vacuo. The crude product was purified by chromatography on silica gel, eluting with a solvent gradient of 0.880 aqueous ammonia:methanol:dichloromethane (0:8:25 to 0:5:8:25), to furnish the title compound (112 mg) as a solid, m.p. 168°–169° C. Found: C,75.66; H,8.34; N,8.57. $C_{20}H_{26}N_2O$; 0.10 $CH_2Cl_2$ requires C,75.36; H,8.28; N,8.78%. LRMS: m/z 311.2 $(M+1)^+$.

EXAMPLE 104

3-[4-(1-Benzyl-1,2,5,6-tetrahydropyridyl)]-5-[2-(1-hydroxycyclopentyl)ethyl]-1H-indole Obtained from the product of Example 103(b) and 1-benzyl-4-piperidone, by a procedure similar to that described in Example 103(c), as a solid. Rf 0.65 (SS 7). Found: C,78.87; H,7.78; N,6.85. $C_{27}H_{32}N_2O$; 0.10 $CH_2Cl_2$; 0.17 $H_2O$ requires C,78.73; H,7.95; N,6.80%. LRMS: m/z 401.6 $(M+1)^+$.

EXAMPLE 105

5-[2-(1-Hydroxycyclopentyl)ethyl]-3-(4-piperidyl)-1H-indole

Obtained from the title compound of Example 104 by a procedure similar to that described in Example 2, but using 10% palladium on charcoal as catalyst, as a solid, m.p. 190°–191° C. Found: C,71.26; H,8.72; N,8.04. $C_{20}H_{28}N_2O$; 0.30 $CH_2Cl_2$ requires C,71.22; H,8.53; N,8.29%. LRMS: m/z 313.3 $(M+1)^+$.

EXAMPLE 106

3-[2-(N-Benzyl-N-methylamino)ethyl]-5-[2-(1-hydroxycyclopentyl)ethenyl]-1H-indole (a) N-Benzyl-N-methyl-5-bromo-3-indolylglyoxylamide Oxalyl chloride (2.24 ml, 25 mmol) was added dropwise to a stirred solution of 5-bromoindole (5.0 g, 25 mmol) in anhydrous tetrahydrofuran (60 ml) under nitrogen at room temperature. After 2 hours the reaction mixture was ice-cooled and a solution of N-methylbenzylamine (10.8 g, 89 mmol) in anhydrous tetrahydrofuran (15 ml) added dropwise, then the resulting mixture was stirred for a further 2 hours at 0°–5° C. and partitioned between ethyl acetate and 2M hydrochloric acid. The organic phase was washed with 2M hydrochloric acid and then water, dried ($Na_2SO_4$) and evaporated under reduced pressure to give a solid which was triturated with a 1:2 mixture of hexane:ether, washed with ether (×3) and dried in vacuo, to afford the required product (7.02 g) as a solid. Rf 0.60 (SS 7). Found: C,57.65; H,4.02; N,7.50. $C_{18}H_{15}BrN_2O_2$; 0.33 $H_2O$ requires C,57.30; H,4.16; N,7.42%.

(b) 3-[2-(N-Benzyl-N-methylamino)ethyl]-5-bromo-1H-indole

A solution of the previous product (Example 106(a); 7.0 g, 18 mmol) in anhydrous tetrahydrofuran (50 ml) was added dropwise, over 10 minutes, to a stirred suspension of lithium aluminium hydride (2.0 g, 53 mmol) in anhydrous tetrahydrofuran (50 ml) under nitrogen, then the resulting mixture heated under reflux for 4 hours, allowed to cool and stirred for a further 18 hours at room temperature. The reaction mixture was ice-cooled, carefully quenched by the sequential dropwise addition of water (2 ml), 4M aqueous sodium hydroxide solution (2 ml) and water (6 ml), then filtered. The filtrate was evaporated under reduced pressure and the residue azeotroped with dichloromethane to give a product which, by spectral analysis (infra red and $^1H$ NMR), was shown to contain partially reduced material.

Thus further treatment with lithium aluminium hydride (4.0 g, 106 mmol) in anhydrous tetrahydrofuran (50 ml) at reflux temperature for 18 hours was effected and the resulting reaction mixture worked up as before. Purification of the residue by column chromatography on silica gel, eluting with a solvent gradient of ethanol: dichloromethane (0:100 to 0.5:99.5 to 3:97), yielded the required product (2.67 g) as an oil. Found: C,64.51; H,5.85; N,8.26. $C_{18}H_{19}BrN_2$; 0.10 $CH_2Cl_2$ requires C,64.51; H,5.78; N,8.32%. LRMS: m/z 343.0 $(^{79}Br\ M+1)^+$ and 345.0 $(^{81}Br\ M+1)^+$.

(c)

The title compound was obtained from the previous product (Example 106(b)) and the product of Example 5(a), by a procedure similar to that described in Example 1, as a foam. Rf 0.64 (SS 7). Found: C,78.53; H,8.00; N,7.38. $C_{25}H_{30}N_2O$; 0.10 $CH_2Cl_2$ requires C,78.39; H,7.95; N,7.32%. LRMS: m/z 375.3 $(M+1)^+$.

EXAMPLE 107

5-[2-(1-Hydroxycyclopentyl)ethyl]-3-[2-(N-methyl amino)ethyl]-1H-indole

Obtained from the title compound of Example 106 by a procedure similar to that described in Example 2, but using 10% palladium on charcoal as catalyst, as a foam. Rf 0.06 (SS 7). Found: C,71.90; H,8.88; N,9.15. $C_{18}H_{26}N_2O$; 0.08 $CH_2Cl_2$; 0.50 $H_2O$ requires C,71.49; H,9.05; N,9.26%. LRMS: m/z 287.6 $(M+1)^+$.

EXAMPLE 108

3-(N-Benzyl-3-pyrrolidinyl)-5-[2-(1-hydroxycyclopentyl)ethenyl]-1H-indole (a) 3-(N-Benzyl-3-succinimidyl)-5-bromo-1H-indole A stirred mixture of 5-bromoindole (8.0 g, 41 mmol), N-benzylmaleimide (8.13 g, 45 mmol) and glacial acetic acid, under nitrogen, was heated under reflux for 48 hours and then evaporated under reduced pressure. Residual solvent was removed azeotropically using toluene (2×50 ml) and then ethyl acetate (2×50 ml), then the residue was purified by column chromatography on silica gel, eluting with a solvent gradient of ethyl acetate:hexane (1:3 to 2:3), to furnish the required product (11.49 g) as a solid, m.p. 169°–170° C. Rf 0.04 (SS 5). Found: C,59.74; H,3.87; N,7.07. $C_{19}H_{15}BrN_2O_2$ requires C,59.54; H,3.94; N,7.31%.

(b) 3-(N-Benzyl-3-pyrrolidinyl)-5-bromo-1H-indole

A solution of the previous product (Example 108(a); 3.80 g, 9.9 mmol) in anhydrous tetrahydrofuran (50 ml) was added dropwise to a stirred suspension of lithium aluminium hydride (2.26 g, 59 mmol) in anhydrous tetrahydrofuran (50 ml) under nitrogen and the resulting mixture heated under reflux for 22 hours. The ice-cooled reaction mixture was cautiously quenched by the sequential dropwise addition of water (2.26 ml), 4M aqueous sodium hydroxide solution (2.26 ml) and more water (6.78 ml), then filtered. The filtrate was evaporated under reduced pressure, then the residue azeotroped with dichloromethane and purified by chromatography on silica gel, eluting with a solvent gradient of ethanol:dichloromethane (0:100 to 4:96), to provide the required product (2.18 g) as a foam. Rf 0.44 (SS 7). LRMS: m/z 355.0 ($^{79}$Br M+1)$^+$ and 357.0 ($^{81}$Br M+1)$^+$.

(c)

The title compound was obtained from the previous product (Example 108(b)) and the product of Example 5(a), by a procedure similar to that described in Example 1, as a foam. Rf 0.51 (SS 7). Found: C,79.08; H,7.71; N,6.97. $C_{26}H_{30}N_2O$; 0.08.$CH_2Cl_2$ requires C,79.41; H,7.72; N,7.12%. LRMS: m/z 387.0 (M+1)$^+$.

EXAMPLE 109

5-[2-(1-Hydroxycyclopentyl)ethyl]-3-(3-pyrrolidinyl)-1H-indole

The title compound was obtained from the title compound of Example 108 using a procedure similar to that described in Example 2, but using 10% palladium on charcoal as catalyst, as a foam. Rf 0.04 (SS 7). Found: C,71.39; H,8.96; N,8.12. $C_{19}H_{26}N_2O$; 0.50 $CH_3CH_2OH$; 0.10 $H_2O$ requires C,70.90; H,9.09; N,8.67%. LRMS: m/z 299.1 (M+1)$^+$.

PREPARATION 1

3-(N-Benzyloxycarbonyl-2(R)-pyrrolidinylmethyl)-5-bromo-1H-indole 3-(N-Benzyloxycarbonyl-2(R)-pyrrolidinylcarbonyl)-5-bromo-1H-indole (WO-A-92/06973; 0.67 g, 1.57 mmol) was dissolved in dry tetrahydrofuran (20 ml) and, at room temperature under nitrogen, lithium borohydride (2M solution in tetrahydrofuran; 1.2 ml, 2.4 mmol) was added. The reaction mixture was stirred at room temperature for 3 hours, heated under reflux for 16 hours, then allowed to cool to room temperature. 2M Hydrochloric acid (10 ml) was added dropwise and the reaction mixture then partitioned between ethyl acetate and water. The separated organic phase was washed with saturated aqueous sodium bicarbonate solution (×2) and brine (×1), dried ($Na_2SO_4$), and evaporated under reduced pressure to give a colourless oil. Purification by column chromatography on silica gel, eluting with dichloromethane, gave the title compound as an oil (0.32 g). Rf 0.20 (SS 16). Found: C,59.94; H,5.07; N,6.58. $C_{21}H_{21}BrN_2O_2$; 0.10 $CH_2Cl_2$ requires C,60.08; H,5.07; N,6.64%. δ($CDCl_3$)—mixture of rotamers: 1.63–1.90 (4H, m), 2.60–2.82 (1H, m), 3.10–3.28 (1H, m), 3.30–3.54 (2H, m), 4.18 (1H, m), 5.15–5.25 (2H, m), 5.30 (0.2H, s, $CH_2Cl_2$), 6.90 and 6.95 (1H, 2×s), 7.05–7.50 (7H, m), 7.70 and 7.85 (1H, 2×s), 8.25 (1H, br s).

PREPARATION 2

5-Bromo-3-(2(R)-pyrrolidinylmethyl)-1H-indole

The title compound was prepared by any of the following methods.

(A)

A mixture of the title compound of Preparation 1 (10.0 g, 24.2 mmol) and a solution of hydrogen bromide in glacial acetic acid (36% w/w; 17 ml) was stirred at about 0° C. for 1 hour, then the solvent removed under reduced pressure and the residue azeotroped with toluene. The resulting oil was partitioned between dichloromethane and 2M aqueous sodium carbonate solution, then the organic phase separated, combined with a further dichloromethane extract of the aqueous phase, dried ($Na_2SO_4$) and evaporated under reduced pressure. Purification of the crude product by column chromatography on silica gel, eluting with a solvent gradient of 0.880 aqueous ammonia:methanol: dichloromethane (0:5:95 to 2:5:95), gave the title compound as an oil (2.01 g). Rf 0.10 (SS 7). [α]$_D^{25}$–9° (c=0.1, $CH_3OH$). Found: C,54.75; H,5.41; N,9.63. $C_{13}H_{15}BrN_2$; 0.20 $CH_2Cl_2$ requires C,54.84; H,5.37; N,9.67%.

(B)

A solution of the title compound of Preparation 1 (5.0 g, 12.1 mmol) in dichloromethane was added dropwise to a stirred mixture of boron trifluoride etherate (17.15 g, 14.9 ml, 12.1 mmol) and ethanethiol (21.4 g, 25.5 ml, 344 mmol) at room temperature under nitrogen. After 68 hours the reaction mixture was poured into 10% aqueous sodium carbonate solution, then extraction with ethyl acetate (3×400 ml) effected. Evaporation under reduced pressure of the dried ($Na_2SO_4$), combined extracts, followed by column chromatography on silica gel of the crude product, eluting with 0.880 aqueous ammonia:methanol: dichloromethane (1:10:90), provided the title compound as a foam (2.10 g). Rf 0.10 (SS 7). [α]$_D^{25}$–12° (c=0.1, $CH_3OH$). Found: C,55.04; H,5.29; N,9.83. $C_{13}H_{15}BrN_2$; 0.06 $CH_2Cl_2$ requires C,55.10; H,5.35; N,9.83%.

(C)

A saturated solution of hydrogen chloride in methanol (20 ml) was added to a stirred, ice-cooled solution of the title compound of Preparation 1 (10.0 g, 24.2 mmol) in dichloromethane (20 ml) under nitrogen. After 1 hour the ice bath was removed and the reaction mixture stirred at room temperature for 48 hours and then evaporated under reduced pressure. The residual oil was triturated with ether (2×20 ml), then partitioned between ether (50 ml) and water (50 ml). The aqueous phase was washed with ether (2×75 ml), basified with solid sodium carbonate and extracted with ethyl acetate (2×75 ml), then the combined extracts washed with saturated brine, dried ($Na_2SO_4$) and evaporated under reduced pressure. The residue was purified by column chromatography on silica gel, eluting with a solvent gradient of 0.880 aqueous ammonia:methanol:dichloromethane (0:0:100 to 0:10:90 to 1:10:90), to afford the title compound as a solid, m.p. 120°–123.5° C. Rf 0.15 (SS 7). Found: C,55.06; H,5.33; N,9.59. $C_{13}H_{15}BrN_2$; 0.25 $H_2O$ requires C,55.04; H,5.51; N,9.88%.

(D)

A stirred solution of the title compound of Preparation 1 (360 mg, 0.87 mmol) and potassium hydroxide (1.0 g, 17.8 mmol) in ethanol (20 ml) was heated under reflux for 72 hours. The ethanol was removed by evaporation under reduced pressure and replaced with n-butanol (20 ml), then the resulting mixture stirred under reflux for a further 48 hours and evaporated under reduced pressure. The residue was purified as in (C) above to provide the title compound (73 mg). Rf 0.10 (SS 7).

Biological Activity

The following Table illustrates the in vitro activities for a range of the compounds of the invention on dog isolated saphenous vein strip. EC$_{50}$ represents the concentration of compound which causes 50% of the maximum contraction effected by it.

TABLE

| EXAMPLE | $EC_{50}$ (M) | RELATIVE POTENCY $EC_{50}$ (compound) $EC_{50}$ (5-HT) |
|---|---|---|
| 1 | $4.0 \times 10^{-7}$ | 7.7 |
| 25 | $4.8 \times 10^{-7}$ | 6.4 |
| 29 | $6.7 \times 10^{-7}$ | 9.0 |
| 30 | $9.4 \times 10^{-7}$ | 7.2 |
| 37 | $1.3 \times 10^{-7}$ | 1.3 |
| 43 | $5.6 \times 10^{-7}$ | 8.0 |
| 48 | $3.0 \times 10^{-7}$ | 3.2 |
| 95 | $3.2 \times 10^{-7}$ | 4.0 |
| 101 | $7.0 \times 10^{-7}$ | 10.0 |
| 109 | $7.5 \times 10^{-7}$ | 8.5 |

Safety Profile

Several of the compounds of the invention have been tested in conscious animals, for example Examples and 29, and showed no signs of adverse acute toxicity at doses of up to 1 mg/Kg i.v. in dog and up to 10 mg/Kg i.v. in mouse.

I claim:

1. A compound of formula (I):

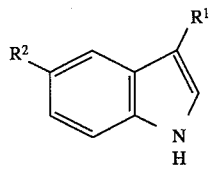

or a pharmaceutically acceptable salt thereof, or a pharmaceutically acceptable solvate of either entity, wherein $R^1$ is

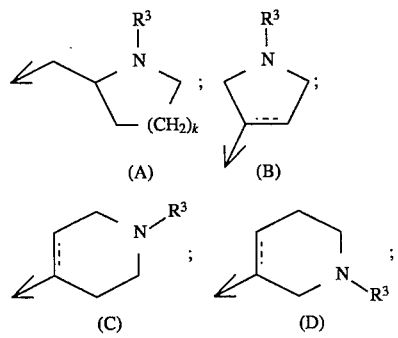

or $CH_2CH_2NR^3R^4$ (E);

$R^2$ is $R^5R^6C(OH)A$ or $R^7COA$; $R^3$ is H; $C_1-C_6$ alkyl; $(R^8CO)$ $C_1-C_3$ alkylene; $(R^9O_2C)$ $C_1-C_3$ alkylene; $(R^{10}R^{11}NOC)$ $C_1-C_6$ alkylene; $(R^{10}R^{11}NO_2S)$ $C_1-C_3$ alkylene; $[R^8S(O)_m]C_1-C_3$ alkylene; $(R^{12}O)$ $C_2-C_4$ alkylene; $(R^{13}NH)$ $C_2-C_4$ alkylene; $(C_3-C_7$ cycloalkyl) $C_1-C_3$ alkylene; (aryl) $C_1-C_3$ alkylene; (heteroaryl) $C_1-C_3$ alkylene; $C_3-C_7$ cycloalkyl optionally substituted with HO; $C_3-C_6$ alkenyl optionally substituted with aryl; $C_5-C_7$ cycloalkenyl; or $C_3-C_6$ alkynyl;

$R^4$ is H or $C_1-C_6$ alkyl;

$R^5$ and $R^6$ are each independently selected from H; $C_1-C_6$ alkyl; $C_1-C_4$ perfluoroalkyl; and $C_3-C_7$ cycloalkyl; or, together with the carbon atom to which they are attached, form a 3- to 7-membered carbocyclic ring which optionally incorporates a double bond or a heteroatom linkage selected from O, $S(O)_m$, NH, $N(C_1-C_4$ alkyl), and $N(C_1-C_5$ alkanoyl);

$R^7$ and $R^8$ are each independently selected from $C_1-C_6$ alkyl; $(C_3-C_7$ cycloalkyl) $C_1-C_3$ alkylene; (aryl) $C_1-C_3$ alkylene; $C_3-C_7$ cycloalkyl; and aryl;

$R^9$ is $C_1-C_6$ alkyl; $(C_3-C_7$ cycloalkyl) $C_1-C_3$ alkylene; (aryl) $C_1-C_3$ alkylene; or $C_3-C_7$ cycloalkyl;

$R^{10}$ and $R^{11}$ are each independently selected from H; $C_1-C_6$ alkyl; $(R^{14}R^{15}NOC)$ $C_1-C_3$ alkylene; $(R^{16}O)$ $C_2-C_4$ alkylene; $(C_3-C_7$ cycloalkyl) $C_1-C_3$ alkylene; (aryl) $C_1-C_3$ alkylene; and $C_3-C_7$ cycloalkyl; or, together with the nitrogen atom to which they are attached, form a 4- to 7-membered heterocyclic ring which optionally incorporates a further heteroatom linkage selected from O, $S(O)_m$, NH, $N(C_1-C_4$ alkyl), and $N(C_1-C_5$ alkanoyl);

$R^{12}$ is H; $C_1-C_6$ alkyl; $(C_3-C_7$ cycloalkyl) $C_1-C_3$ alkylene; (aryl) $C_1-C_3$ alkylene; $C_3-C_7$ cycloalkyl; or aryl;

$R^{13}$ is H; $C_1-C_5$ alkanoyl; $(C_1-C_4$ alkyl)$SO_2$; or $H_2NSO_2$;

$R^{14}$ and $R^{15}$ are each independently selected from H or $C_1-C_4$ alkyl;

$R^{16}$ is H; $C_1-C_4$ alkyl; or benzyl;

A is a direct link; $C_1-C_6$ alkylene optionally branched with $C_1-C_4$ alkyl; or $C_2-C_6$ alkenylene optionally branched with $C_1-C_4$ alkyl;

k and m are each independently selected from 0, 1 and 2; and the broken line indicates an optional carbon-carbon single bond;

with the proviso that, for a compound of formula (IE) wherein $R^2$ is $R^7COA$ and A is a direct link, $R^7$ is not (a) methyl, ethyl, phenyl or 4-chlorophenyl when both $R^3$ and $R^4$ are H;

(b) methyl when both $R^3$ and $R^4$ are methyl; or (c) phenyl when both $R^3$ and $R^4$ are ethyl, or when either of $R^3$ and $R^4$ is ethyl or butyl and the other is H.

2. A compound according to claim 1 of formula (IA) wherein $R^2$ is $R^5R^6C(OH)A$ or $R^7COA$; $R^3$ is H; $C_1-C_4$ alkyl; (benzyl$O_2C$) $C_1-C_3$ alkylene; $(R^{10}R^{11}NOC)$ $C_1-C_6$ alkylene; $(R^{10}R^{11}NO_2S)$ $C_1-C_3$ alkylene; $(R^8SO_2)$ $C_1-C_3$ alkylene; $(R^{12}O)$ $C_2-C_4$ alkylene; $(R^{13}NH)$ $C_2-C_4$ alkylene; $(C_4-C_6$ cycloalkyl) $C_1-C_3$ alkylene; or (pyridyl) $C_1-C_3$ alkylene; $R^5$ and $R^6$ are each independently selected from H; $C_1-C_4$ alkyl; $CF_3$; and cyclopentyl; or, together with the carbon atom to which they are attached, form a 4- to 6-membered carbocyclic ring which optionally incorporates an oxygen atom linkage; $R^7$ is $C_1-C_4$ alkyl or $C_4-C_6$ cycloalkyl; $R^8$ is $C_1-C_4$ alkyl; $R^{10}$ and $R^{11}$ are each independently selected from H; $C_1-C_4$ alkyl; $(R^{14}R^{15}NOC)$ $C_1-C_3$ alkylene; and $(R^{16}O)$ $C_2-C_4$ alkylene; or, together with the nitrogen atom to which they are attached, form a 5- to 6-membered heterocyclic ring which optionally incorporates an oxygen atom linkage; $R^{12}$ is H; $C_1-C_4$ alkyl; or benzyl; A is a direct link; $C_1-C_4$ alkylene; or $C_2-C_4$ alkenylene; k is 1; and $R^{13}$, $R^{14}$, $R^{15}$ and $R^{16}$ are as previously defined for formula (IA); of formula (IB) wherein $R^2$ is $R^5R^6C(OH)A$; $R^3$ is H or benzyl; $R^5$ and $R^6$ together with the carbon atom to which they are attached form a 4- to 6-membered carbocyclic ring; A is ethylene or vinyl; and the broken line is absent; of formula (IC) wherein $R^2$ is $R^5R^6C(OH)A$ or $R^7COA$; $R^3$ is H, $C_1-C_4$ alkyl or benzyl; $R^5$ and $R^6$ are each independently selected from H and $C_1-C_4$ alkyl; or, together with the carbon atom to which they are attached, form a 4- to 6-membered carbocyclic ring; $R^7$ is $C_1-C_4$ alkyl; A is a direct link; ethylene or vinyl; and the broken line indicates an optional carbon-carbon single bond; .and of formula (IE): wherein $R^2$ is $R^5R^6C(OH)A$; $R^3$ and $R^4$ are each independently selected from H, $C_1-C_4$ alkyl and benzyl; $R^5$ and $R^6$ are each $C_1-C_4$ alkyl or, together with the carbon atom to which they are attached, form a 4- to 6-membered carbocyclic ring; and A is ethylene or vinyl.

3. A compound according to claim 2 of formula (IA) wherein $R^2$ is $R^5R^6C(OH)A$ or $R^7COA$; $R^3$ is H; $C_1$–$C_3$ alkyl; $(R^{10}R^{11}NOC)$ $C_1$–$C_5$ alkylene; $CH_3NHO_2SCH_2CH_2$; $CH_3OCH_2CH_2$; or $(cyclopropyl)CH_2$; $R^5$ is methyl, $R^6$ is H, methyl, ethyl or $CF_3$, or $R^5$ and $R^6$ together with the carbon atom to which they are attached, form a cyclobutyl, cyclopentyl or 3-tetrahydrofuranyl ring; $R^7$ is methyl; $R^{10}$ and $R^{11}$ are each independently selected from H; methyl; $(CH_3)_2NOCCH_2$; $(CH_3)_2NOCCH_2CH_2$; $HOCH_2CH_2$; and $CH_3OCH_2CH_2$; and A is ethylene, propylene or vinyl; of formula (IC) wherein $R^2$ is $R^5R^6C(OH)A$; $R^3$ is H or methyl; $R^5$ is methyl, $R^6$ is H or methyl, or $R^5$ and $R^6$ together with the carbon atom to which they are attached form a cyclopentyl ring; A is ethylene or vinyl; and the broken line indicates an optional carbon-carbon single bond; and of formula (IE) wherein $R^2$ is $R^5R^6C(OH)CH_2CH_2$; $R^3$ is methyl; $R^4$ is H; and $R^5$ and $R^6$ together with the carbon atom to which they are attached form a cyclopentyl ring.

4. A compound according to claim 3 of formula (IA) wherein $R^2$ is $R^5R^6C(OH)A$; $R^3$ is H; methyl; 2-propyl; $CH_3NHOCCH_2$; $(CH_3)_2NOCCH_2CH_2$; $CH_3NHOCCH_2CH_2$; $CH_3NHOCCH_2CH_2CH_2$; $CH_3NHOCCH_2CH_2CH_2CH_2$; $HOCH_2CH_2NHOCCH_2CH_2$; $CH_3OCH_2CH_2$ or $(cyclopropyl)CH_2$; $R^5$ is methyl, $R^6$ is H, methyl or $CF_3$, or $R^5$ and $R^6$ together with the carbon atom to which they are attached form a cyclobutyl or cyclopentyl ring; and A is ethylene or vinyl; and of formula (IC) wherein $R^2$ is $CH_3CH(OH)CH_2CH_2$; $R^3$ is methyl; and the broken line is absent.

5. A compound according to claim 1 of formula (IA) wherein the preferred stereoisomer has the 2 (R) -configuration of formula (IA'):

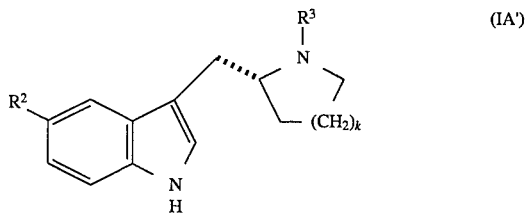

wherein $R^2$, $R^3$ and k are as previously defined in said claims.

6. A compound according to claim 5 wherein the compound of formula (IA') is selected from 5-(3-hydroxy-1-butyl)-3-(N-methyl-2(R)-pyrrolidinylmethyl)-1H-indole;

3-(N-cyclopropylmethyl-2(R)-pyrrolidinylmethyl)-5-(3-hydroxy-3-methyl-1-butyl)-1H-indole;

5-[2-(1-hydroxycyclopentyl)ethyl]-3-(2(R)-pyrrolidinylmethyl)-1H-indole;

5-[2-(1-hydroxycyclopentyl)ethyl]-3-(N-methyl-2(R)-pyrrolidinylmethyl)-1H-indole;

5-[2-(1-hydroxycyclopentyl)ethyl]-3-{N-[2-(N-methylcarbamoyl)ethyl]-2(R)-pyrrolidinylmethyl}-1H-indole; and 5-[2-(1-hydroxycyclopentyl)ethyl]-3-{N-[2-(N,N-dimethylcarbamoyl)ethyl]-2(R)-pyrrolidinylmethyl}-1H-indole.

7. A pharmaceutical composition for treating a condition selected from migraine, cluster headache, chronic paroxysmal hemicrania or headache associated with a vascular disorder, depression, anxiety, an eating disorder, obesity, drug abuse, and emesis comprising an amount of a compound according to claim 1 effective in treating such a condition together with a pharmaceutically acceptable diluent or carrier.

8. A method of treating a human being for a condition selected from migraine, cluster headache, chronic paroxysmal hemicrania or headache associated with a vascular disorder, depression, anxiety, an eating disorder, obesity, drug abuse or emesis, which comprises treating said human being with an effective amount of a compound according to claim 1.

9. A method of treating a human being for medical condition for which a selective agonist of 5-$HT_1$-like receptors is indicated, which comprises treating said human being with an effective amount of a compound according to claim 1.

* * * * *